US010299995B2

(12) United States Patent
Hiramatsu et al.

(10) Patent No.: US 10,299,995 B2
(45) Date of Patent: May 28, 2019

(54) METHOD FOR PRODUCING HYDROGEL PARTICLES

(71) Applicant: KAO CORPORATION, Tokyo (JP)

(72) Inventors: Shinobu Hiramatsu, Wakayama (JP); Katsutake Uehiro, Wakayama (JP); Masanori Orita, Chiba (JP); Kimikazu Fukuda, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/577,546

(22) PCT Filed: May 27, 2016

(86) PCT No.: PCT/JP2016/065736
§ 371 (c)(1),
(2) Date: Nov. 28, 2017

(87) PCT Pub. No.: WO2016/194817
PCT Pub. Date: Dec. 8, 2016

(65) Prior Publication Data
US 2018/0168940 A1    Jun. 21, 2018

(30) Foreign Application Priority Data

May 29, 2015   (JP) .................................. 2015-110876

(51) Int. Cl.
*A61K 8/04*      (2006.01)
*A61Q 19/00*     (2006.01)
(Continued)

(52) U.S. Cl.
CPC ............ *A61K 8/042* (2013.01); *A61K 8/0216* (2013.01); *A61K 8/0241* (2013.01); *A61K 8/73* (2013.01);
(Continued)

(58) Field of Classification Search
CPC ....... A61K 8/042; A61K 8/0241; B01J 13/00; A61Q 17/04
See application file for complete search history.

(56) References Cited

U.S. PATENT DOCUMENTS 6,391,288 B1   5/2002   Miyazawa et al.
2002/0034525 A1   3/2002   Sakai et al.
(Continued)

FOREIGN PATENT DOCUMENTS

FR      2722524 A1    1/1996
GB      1491023 A     11/1977
(Continued)

OTHER PUBLICATIONS

International Search Report for PCT/JP2016/065736 dated Jul. 26, 2016.
(Continued)

*Primary Examiner* — Carlos A Azpuru
(74) *Attorney, Agent, or Firm* — Birch, Stewart, Kolasch & Birch, LLP

(57) ABSTRACT

Disclosed herein is a method for producing hydrogel particles including the steps of: solidifying an aqueous solution in which a gel agent forming a non-crosslinked hydrogel is dissolved and which has a gel point of 30° C. or more by putting the aqueous solution into a liquid phase having a temperature of equal to or lower than the gel point; and crushing a solidified product obtained by solidifying the aqueous solution in which the gel agent is dissolved.

15 Claims, 2 Drawing Sheets

(51) Int. Cl.
  *A61Q 17/04* (2006.01)
  *B01J 13/00* (2006.01)
  *A61K 8/73* (2006.01)
  *A61K 8/02* (2006.01)

(52) U.S. Cl.
  CPC ............ *A61Q 17/04* (2013.01); *A61Q 19/00* (2013.01); *B01J 13/0065* (2013.01); *A61K 2800/10* (2013.01)

(56) References Cited

U.S. PATENT DOCUMENTS

| | | |
|---|---|---|
| 2002/0086042 A1 | 7/2002 | Delrieu et al. |
| 2003/0072805 A1 | 4/2003 | Miyazawa et al. |
| 2009/0047312 A1 | 2/2009 | Miyazawa et al. |
| 2009/0163607 A1 | 6/2009 | Mine et al. |
| 2012/0124725 A1 | 5/2012 | Ballestra |
| 2012/0288457 A1 | 11/2012 | Onishi et al. |

FOREIGN PATENT DOCUMENTS

| | | | |
|---|---|---|---|
| JP | 2000-86407 A | | 3/2000 |
| JP | 2001-97818 A | | 4/2001 |
| JP | 2001-342451 A | | 12/2001 |
| JP | 2002-58990 A | | 2/2002 |
| JP | 2002-159838 A | | 6/2002 |
| JP | 2003-512923 A | | 4/2003 |
| JP | 2003512923 | * | 4/2003 |
| JP | 2003-267829 A | | 9/2003 |
| JP | 2007-160277 A | | 6/2007 |

OTHER PUBLICATIONS

English translation of the International Preliminary Report on Patentability and Written Opinion of the International Searching Authority (Forms PCT/IB/373 and PCT/ISA/237) dated Dec. 5, 2017, for International Application No. PCT/JP2016/065736.
Extended European Search Report dated Dec. 14, 2018, for European Application No. 16803252.2.

* cited by examiner

HYDROGEL PARTICLES

METHOD FOR PRODUCING HYDROGEL PARTICLES

TECHNICAL FIELD

The present invention relates to a method for producing hydrogel particles, a method for producing a cosmetic product, and an apparatus for use in these methods.

BACKGROUND ART

It has been known that hydrogel particles, in which dispersed particles including various kinds of functional materials are distributed, are applicable to cosmetic products, drugs, quasi drugs, and other products.

Patent Document 1, for example, discloses a method for producing such hydrogel particles in which a dispersion, containing an oil component dispersed in an aqueous component solution of dissolved gel agent forming a non-crosslinked hydrogel, is prepared and sprayed into a gas phase to form droplets, which are then cooled and allowed to solidify.

Patent Document 2 discloses preparing an O/W/O emulsion by dispersing, in an external oil phase, an O/W emulsion produced from an internal oil phase and an aqueous phase including a hydrophilic polymer gel agent, and then cooling the O/W/O emulsion to solidify the aqueous phase.

Meanwhile, Patent Document 3 discloses a method of making a thickener including the step of preparing an aqueous solution in which a hydrophilic compound with a gelling capability is dissolved in either water or an aqueous component, leaving it to stand still and cool to form a gel, and then pulverizing the gel.

CITATION LIST

Patent Documents

Patent Document 1: Japanese Unexamined Patent Publication No. 2007-160277
Patent Document 2: Japanese Unexamined Patent Publication No. 2001-97818
Patent Document 3: Japanese Unexamined Patent Publication No. 2001-342451

SUMMARY

A method for producing hydrogel particles according to the present invention includes the steps of: solidifying an aqueous solution in which a gel agent forming a non-crosslinked hydrogel is dissolved and which has a gel point of 30° C. or more by putting the aqueous solution into a liquid phase having a temperature of equal to or lower than the gel point; and crushing a solidified product obtained by solidifying the aqueous solution in which the gel agent is dissolved.

A method for producing a cosmetic product according to the present invention includes the steps of: solidifying an aqueous solution in which a gel agent forming a non-crosslinked hydrogel is dissolved and which has a gel point of 30° C. or more by putting the aqueous solution into a liquid phase having a temperature of equal to or lower than the gel point; and crushing a solidified product included in the liquid phase and obtained by solidifying the aqueous solution in which the gel agent is dissolved.

An apparatus according to the present invention is an apparatus for producing hydrogel particles of a non-crosslinked hydrogel or a cosmetic product including the hydrogel particles. The apparatus includes: a pipe configured to allow a liquid phase, including a solidified product obtained by cooling and solidifying an aqueous solution in which a gel agent, forming the non-crosslinked hydrogel, is dissolved, to flow therethrough; and a solidified product crushing member provided halfway through the pipe.

DESCRIPTION OF EMBODIMENTS

Figure 1:
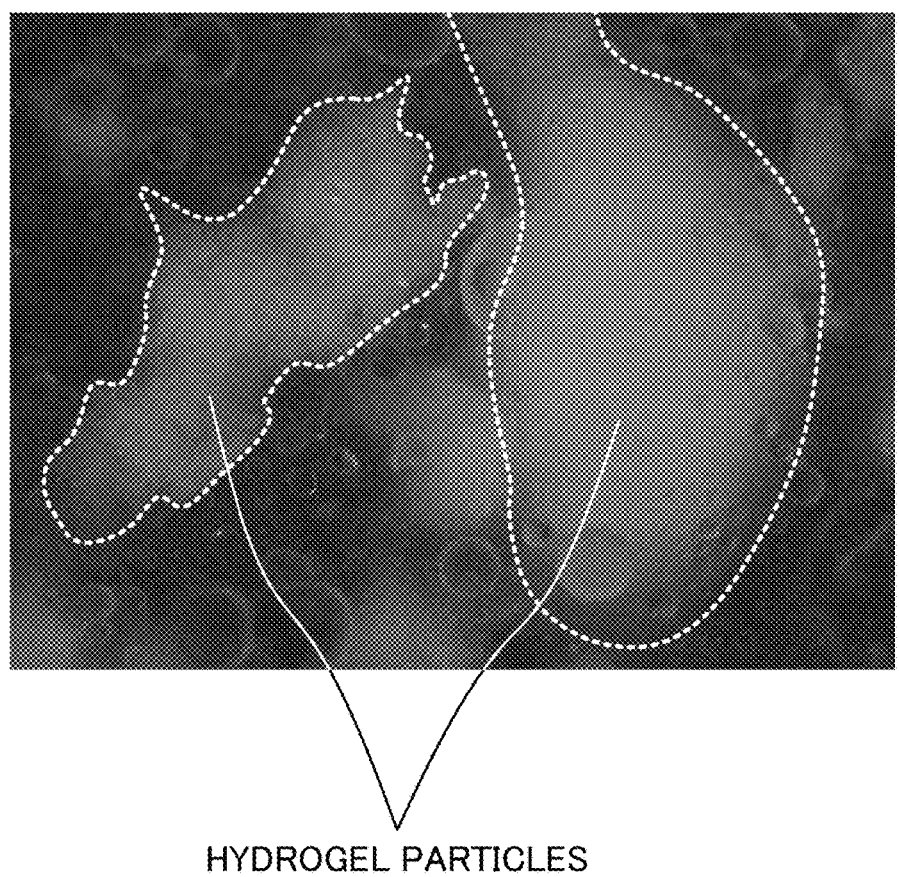
FIG. 1 A microphotograph of hydrogel particles.

Embodiments will be described in detail below.

A method for producing hydrogel particles according to an embodiment includes the steps of: solidifying an aqueous solution in which a gel agent forming a non-crosslinked hydrogel is dissolved and which has a gel point of 30° C. or more (hereinafter referred to as a "gel agent aqueous solution") by putting the aqueous solution into a liquid phase having a temperature of equal to or lower than the gel point; and crushing a solidified product obtained by solidifying the aqueous solution in which the gel agent is dissolved. Such a method for producing hydrogel particles according to an embodiment includes crushing a solidified product obtained by putting a gel agent aqueous solution into a liquid phase and cooling and solidifying the gel agent aqueous solution, thus allowing hydrogel particles to be produced without using any special facility, i.e., by an inexpensive and simple method.

As used herein, the "hydrogel particle(s)" refers to one or more particles of a non-crosslinked hydrogel. The "non-crosslinked hydrogel" refers herein to a gel made from a gel agent and water, and may be a gel resulting from the thermal reversibility of a sol-gel as in a case where the gel agent is agar, for example. The "gel agent" refers herein to a water-soluble organic compound, and is an agent which induces an aqueous solution in which the agent is dissolved in water to cause a sol-gel transition at a gel point (congealing point).

Examples of the gel agent that forms the non-crosslinked hydrogel include water-soluble polymers such as agar, carrageenan, gellan gum, xanthan gum, and high methoxyl pectin. As the gel agent, it is recommended to use one, two, or more of these. Among other things, it is recommended to use agar, in particular. As used herein, the "agar" refers to a hemicellulose containing galactan comprised of 1,3-bond and 1,4-bond of galactose.

Considering that a product such as a cosmetic product, including the hydrogel particles thus obtained, will feel soft in use, the gel agent suitably has a jelly strength of at least equal to 19.6 kPa (200 g/cm$^2$), more suitably equal to or greater than 50 kPa (510 g/cm$^2$). From the same point of view, the jelly strength is suitably at most equal to 147 kPa (1500 g/cm$^2$) and more suitably equal to or less than 127 kPa (1300 g/cm$^2$). The jelly strength of the gel agent is suitably in the range of 19.6-147 kPa (200-1500 g/cm$^2$), and more suitably in the range of 50-127 kPa (510-1300 g/cm$^2$). The jelly strength of a gel agent may be determined by the Nikkansui method. Specifically, the jelly strength of the gel agent may be determined by preparing a 1.5 mass % aqueous solution of the gel agent, making a non-crosslinked hydrogel by leaving the aqueous solution to stand still at 20° C. for 15 hours and solidify, applying a load to the non-crosslinked hydrogel with a Nikkansui-type jelly strength meter (manufactured by KIYA Seisakusho Co. Ltd.), and calculating the maximum mass (g) per surface area of 1 $cm^2$ when the non-crosslinked hydrogel can withstand the load at 20° C. for 20 seconds.

In view of its aptitude for manufacturing, the content of the gel agent in the gel agent aqueous solution is suitably at least equal to 0.1 mass %, more suitably equal to or greater than 0.3 mass %, even more suitably equal to or greater than 0.4 mass %, and yet more suitably equal to or greater than 0.5 mass %. Furthermore, considering that a product such as a cosmetic product, including the hydrogel particles thus obtained, will feel soft in use, the content of the gel agent in the gel agent aqueous solution is suitably at most equal to 8.0 mass %, more suitably equal to or less than 7.0 mass %, even more suitably equal to or less than 6.0 mass %, yet more suitably equal to or less than 5.0 mass %, and most suitably equal to or less than 3.0 mass %. In view of these considerations, the content of the gel agent in the gel agent aqueous solution is suitably in the range of 0.1-8 mass %, more suitably in the range of 0.3-7 mass %, even more suitably in the range of 0.4-6 mass %, yet more suitably in the range of 0.5-5 mass %, and most suitably in the range of 0.5-3 mass %.

From the standpoint of solidification ability at room temperature, the gel agent aqueous solution suitably has a gel point (congealing point) of at least equal to 30° C. Considering its solubility during the manufacturing process, the gel agent aqueous solution suitably has a gel point of at least equal to 50° C., more suitably equal to or less than 45° C. In view of these considerations, the gel point of the gel agent aqueous solution is suitably in the range of 30-50° C., and more suitably in the range of 30-45° C. The gel point of the gel agent aqueous solution may be obtained by taking about 10 ml of the gel agent aqueous solution into a medium-sized test tube (with a diameter of 1.5 cm×16 cm), inserting a thermometer thereto, cooling the aqueous solution while tilting the test tube from time to time, and reading the temperature when the surface no longer moves to be immobilized.

To dissolve the gel agent quickly, the temperature of the gel agent aqueous solution is suitably equal to or higher than the melting temperature of the gel agent and equal to or lower than the boiling point of water. For example, if the gel agent is agar, the temperature of the gel agent aqueous solution is suitably in the range of 75-100° C., and more suitably in the range of 80-100° C. Optionally, to promote the dissolution of the gel agent, the temperature of the gel agent aqueous solution may be raised to 100° C. or more by applying pressure thereto.

From the standpoint of improving the manufacturing efficiency, the temperature of the gel agent aqueous solution being put into the liquid phase is suitably higher than the gel point and equal to or lower than the boiling point of water. For example, if the gel agent is agar, the temperature of the gel agent aqueous solution is suitably at least equal to 40° C., more suitably equal to or higher than 50° C., and even more suitably equal to or higher than 60° C. Meanwhile, the temperature of the gel agent aqueous solution is suitably lower than 100° C., more suitably equal to or lower than 90° C., even more suitably equal to or lower than 80° C., and yet more suitably equal to or lower than 70° C. The temperature of the gel agent aqueous solution being put into the liquid phase is suitably equal to or higher than 40° C. but lower than 100° C., more suitably in the range of 50-80° C., even more suitably in the range of 50-70° C., and yet more suitably in the range of 60-70° C.

The gel agent aqueous solution may be a dispersion in which dispersed particles are distributed. That is to say, the resultant hydrogel particles may have a particle body of a non-crosslinked hydrogel in which dispersed particles are distributed. Examples of the dispersed particles include oil components, water-insoluble complexes including catechins, and powders for cosmetic products.

The oil component is disclosed in detail in Patent Document 1. The dispersed particles of the oil component include at least one of solid fat or liquid oil. As used herein, the "solid fat" refers to an oil and fat having a melting point of equal to or higher than 35° C., while the "liquid oil" refers to an oil and fat having a melting point of lower than 35° C.

Examples of the solid fats include solid ceramides, solid sphingolipids, solid paraffins, solid higher alcohols, vaselines, solid silicones, solid oils, and solid perfumes.

Examples of the solid ceramides include N-(2-hydroxy-3-hexadesiloxypropyl)-N-hydroxyethyl hexadecanamide. Examples of the solid sphingolipids include phytosphingosine. Examples of the solid paraffins include paraffin waxes and microcrystalline waxes listed in JIS K 2235 and ceresin. Examples of the solid higher alcohols include cetyl alcohol, stearyl alcohol, arachidyl alcohol, and behenyl alcohol. Examples of the solid silicones include alkyl-modified silicones and polymeric silicone alkyl co-modified acrylic resin. Examples of the solid oils include hardened oils and higher fatty acids. Examples of the hardened oils include hydrogenated oil, of which the feedstock oil is coconut oil, palm oil or beef tallow. Examples of the higher fatty acids include palmitic acid, behenic acid, and stearic acid. Examples of the solid perfumes include menthol and cedrol.

The content of the solid fat in the dispersed particles of the oil component is suitably at least equal to 1 mass %, more suitably equal to or greater than 6 mass %, even more suitably equal to or greater than 10 mass %, and yet more suitably equal to or greater than 19 mass %. Meanwhile, the content of the solid fat is suitably at most equal to 80 mass %, more suitably equal to or less than 70 mass %, and even more suitably equal to or less than 50 mass %. The content of the solid fat in the dispersed particles of the oil component is suitably in the range of 1-80 mass %, more suitably in the range of 6-80 mass %, even more suitably in the range of 10-70 mass %, and yet more suitably in the range of 19-50 mass %.

Examples of the liquid oils include liquid skin protecting agents, liquid oils, and liquid perfumes.

Examples of the liquid skin protecting agents include: liquid fats such as liquid paraffin, liquid ester oils such as methoxy octyl cinnamate, liquid higher alcohols, liquid squalane and liquid glycerides; liquid ceramides such as cetyloxypropylglyceryl methoxypropyl myristamide; and liquid sphingolipids such as 1-(2-hydroxyethylamino)-3-isostearyloxy-2-propanol. Examples of the liquid oils include: liquid hydrocarbon oils, liquid vegetable oils, liquid fatty acids; liquid oils and fats including liquid ethylene glycol di-fatty acid esters (the number of carbon atoms in the fatty acid is in the range of 12-36) and liquid dialkyl ethers (the number of carbon atoms is in the range of 12-36); and liquid silicones.

To achieve the effect by the liquid oil, the content of the liquid oil in the dispersed particles of the oil component is suitably at least equal to 10 mass %, more suitably equal to or greater than 20 mass %, even more suitably equal to or greater than 30 mass %, and yet more suitably equal to or greater than 50 mass %. Meanwhile, considering that a product such as a cosmetic product, including the hydrogel particles thus obtained, will feel soft in use, the content of the liquid oil in the dispersed particles of the oil component is suitably at most equal to 99 mass %, more suitably equal to or less than 94 mass %, even more suitably equal to or less than 90 mass %, and yet more suitably equal to or less than 81 mass %. In view of these considerations, the content of the liquid oil in the dispersed particles of the oil component is suitably in the range of 55-99 mass %, more suitably in the range of 20-94 mass %, even more suitably in the range of 30-90 mass %, and yet more suitably in the range of 50-81 mass %.

As at least one of the solid fat or liquid oil contained in the dispersed particles of the oil component, it is recommended to use one, two, or more of these.

Dispersed particles of the oil component are not limited to any particular form, but may be a water-in-oil emulsion, for example. Also, examples of the dispersed particles of the oil component include not only solid fats and liquid oils, but also inorganic ultraviolet absorbents such as titanium oxide and zinc oxide; organic ultraviolet absorbents such as bisethylhexyloxyphenol methoxyphenyl triazine, ethylhexyl triazone, diethylamino hydroxybenzoyl hexyl benzoate, dimethoxybenzylidene dioxoimidazolidine octyl propionate, and t-butyl methoxybenzoyl methane; and fat-soluble vitamins such as Vitamin A, Vitamin D, Vitamin E, and Vitamin K.

Water-insoluble complexes containing catechins are disclosed in detail in Japanese Unexamined Patent Publications Nos. 2010-131479 and 2011-136983. Dispersed particles of water-insoluble complexes containing catechins include catechins and polymers that form the water-insoluble complexes with the catechins.

The catechins may be non-polymer catechins, for instance. Examples of the catechins include non-epicatechins such as catechin, gallocatechin, catechin gallate, and gallocatechin gallate; and epicatechins such as epicatechin, epigallocatechin, epicatechin gallate, and epigallocatechin gallate. As catechins, it is recommended to use one, two or more of these.

Examples of the polymers forming water-insoluble complexes with catechins include polyvinylpyrrolidone (PVP), polyvinyl alcohol (PVA), hydroxyethyl cellulose (HEC), methylcellulose (MC), hydroxypropyl cellulose (HPC), hydroxypropyl methylcellulose (HPMC), polyethylene glycol (PEG), polyglycerol fatty acid esters, polyoxyethylene alkyl ethers, polyoxyethylene sorbitan alkyl esters (polyoxyethylene sorbitan fatty acid esters), gelatin, and casein sodium. As the polymer, one, two or more of these is suitably used. Polyvinylpyrrolidone (PVP), hydroxyethyl cellulose (HEC), methylcellulose (MC), hydroxypropyl cellulose (HPC), or polyethylene glycol (PEG) is more suitably used. Polyvinylpyrrolidone (PVP) is particularly suitably used.

Examples of the dispersed particles of powders for cosmetic products include: metal soap powders such as zinc stearate, aluminum stearate, calcium stearate, and zinc myristate; resin powders such as nylon powder, polymethyl methacrylate powder, acrylonitrile-methacrylic acid copolymer powder, vinylidene chloride-methacrylic acid copolymer powder, polystyrene powder, organopolysiloxane elastomer powder, and polymethylsilsesquioxane powder; inorganic powders such as titanium oxide, black titanium oxide, iron blue, ultramarine, red iron oxide, yellow iron oxide, black iron oxide, zinc oxide, aluminum oxide, silicon dioxide, magnesium oxide, zirconium oxide, magnesium carbonate, calcium carbonate, chromium oxide, chromium hydroxide, carbon black, aluminum silicate, magnesium silicate, magnesium aluminum silicate, mica, synthetic mica, synthetic sericite, sericite, talc, kaolin, silicon carbide, barium sulfate, bentonite, smectite, and boron nitride; photoluminescent powders such as bismuth oxychloride, mica titanium, iron oxide coated mica, iron oxide mica titanium, organic pigment treated mica titanium, and aluminum powder; organic powders such as wool powder, silk powder, and microcrystalline cellulose; dye powders such as silica, organic tar-based pigments, and organic dye lake pigments; and composite powders such as particulate titanium oxide-coated mica titanium, particulate zinc oxide-coated mica titanium, barium sulfate-coated mica titanium, titanium oxide-containing silicon dioxide, and zinc oxide-containing silicon dioxide. As the powder for cosmetic products, it is recommended to use one, two, or more of these.

If the gel agent aqueous solution is a dispersion, one of these dispersed particles or two or more of these dispersed particles may be distributed in the dispersion.

To achieve the effect by the dispersed particles, the content of the dispersed particles in the gel agent aqueous solution that is a dispersion is suitably at least equal to 1 mass %, more suitably equal to or greater than 7.5 mass %, and even more suitably equal to or greater than 10 mass %. Meanwhile, considering that a product such as a cosmetic product, including the hydrogel particles thus obtained, will feel soft in use, the content of the dispersed particles in the gel agent aqueous solution is suitably at most equal to 60 mass %, more suitably equal to or less than 55 mass %, and even more suitably equal to or less than 50 mass %. In view of these considerations, the content of the dispersed particles is suitably in the range of 1-60 mass %, more suitably in the range of 7.5-55 mass %, and even more suitably in the range of 10-50 mass %.

The dispersed particles may have a spherical, plate-like, or needle-like particle shape, for example.

In view of safety considerations, the volume mean particle size of the dispersed particles is suitably at least equal to 0.01 µm, more suitably equal to or greater than 0.1 µm, and even more suitably equal to or greater than 1 µm. Meanwhile, considering that a product such as a cosmetic product, including the hydrogel particles thus obtained, will feel soft in use, and taking the aptitude for manufacturing into account, the volume mean particle size of the dispersed particles is suitably at most equal to 100 µm, more suitably equal to or less than 50 µm, and even more suitably equal to or less than 20 µm. In view of these considerations, the volume mean particle size of the dispersed particles is suitably in the range of 0.01-100 µm, more suitably in the range of 0.1-50 µm, and even more suitably in the range of 1-20 µm. The volume mean particle size of the dispersed particles may be measured by a laser diffraction/scattering method with a laser diffraction/scattering particle size analyzer (e.g., LA-920 manufactured by HORIBA, Ltd.).

If the gel agent aqueous solution is a dispersion, the gel agent aqueous solution as a dispersion suitably includes at least one of a dispersant to allow the dispersed particles to be distributed or an emulsifier (hereinafter referred to as a "dispersant or any other additive").

Examples of the dispersants include polymer emulsifying and dispersing agents, anionic surfactants, cationic surfactants, nonionic surfactants, and amphoteric surfactants.

Examples of the polymer emulsifying and dispersing agents include a copolymer of acrylic acid and alkyl methacrylate, a complex in which an amphoteric polymer compound and a higher fatty acid are synthesized together as described in Japanese Unexamined Patent Publication No. H7-100356, water-soluble amphiphilic polymer electrolytes as respectively described in Japanese Unexamined Patent Publications Nos. H8-252447 and H9-141079, water-soluble crosslinked amphiphilic polymer electrolytes as respectively described in Japanese Unexamined Patent Publications Nos. H9-141080 and H9-141081, an acrylate-based copolymer as described in Japanese Unexamined Patent Publication No. H10-53625, polysaccharide derivatives as respectively described in Japanese Patent No. 3329689 and Japanese Unexamined Patent Publications Nos. H10-330401 and H11-106401, synthetic polymer compounds such as polyvinyl pyrrolidone, polyvinyl alcohol and their derivatives, polyacrylamides and ethylene oxide adducts of alkyl phenol formaldehyde condensates, and natural polymer compounds such as Guayagamu, karaya gum, tragacanth gum, gum arabic, arabinogalactan, and casein.

Examples of the anionic surfactants include sodium lauryl sulfate, sodium stearate, and sodium polyoxyethylene lauryl ether phosphate. Examples of the cationic surfactants include lauryl trimethyl ammonium chloride, stearyl amine acetate, and stearyl amine acid. Examples of the nonionic surfactants include sorbitan fatty acid esters, polyoxyethylene sorbitan fatty acid esters, and polyoxyethylene sorbitol fatty acid esters. Examples of the amphoteric surfactants include alkyldimethylamino acetic acid betaine and lecithin.

As the dispersant, it is recommended to use one, two, or more of these.

To stabilize the dispersion and emulsion, the content of the dispersant and other additives in the gel agent aqueous solution that is a dispersion is suitably at least equal to 0.01 mass %, more suitably equal to or greater than 0.05 mass %, and even more suitably equal to or greater than 0.1 mass %. Meanwhile, in view of safety considerations, the content of the dispersant and other additives in the gel agent aqueous solution is suitably at most equal to 5 mass %, more suitably equal to or less than 3 mass %, and even more suitably equal to or less than 1 mass %. In view of these considerations, the content of the dispersant and other additives is suitably in the range of 0.01-5 mass %, more suitably in the range of 0.05-3 mass %, and even more suitably in the range of 0.1-1 mass %.

The gel agent aqueous solution may contain one, two, or more antiseptic agents selected from the group consisting of methyl parahydroxybenzoate, isopropyl methyl phenol, ethanol, phenoxyethanol, dehydroacetic acid and salts thereof. The gel agent aqueous solution may also contain a water-soluble vitamin such as Vitamin B or Vitamin C. In addition to these, the gel agent aqueous solution may further contain one, two, or more selected from the group consisting of moisturizers, antiperspirants, antimicrobial agents, and germicides.

Examples of the liquid that forms the liquid phase into which the gel agent aqueous solution is put include water, liquid oils of silicone, and organic solvents. As the liquid, it is recommended to use one, two, or more of these. Considering that a product such as a cosmetic product, including the hydrogel particles thus obtained, will feel soft in use, the liquid phase is suitably an aqueous phase. As used herein, the "aqueous phase" refers to water, an aqueous solution, or a water dispersion.

Considering that a product such as a cosmetic product, including the hydrogel particles thus obtained, will feel soft in use, the mass ratio of the gel agent aqueous solution to the liquid phase (gel agent aqueous solution/liquid phase) is suitably at least equal to 1/99, more suitably equal to or greater than 3/97, even more suitably equal to or greater than 4/96, and particularly suitably equal to or greater than 5/95. Meanwhile, to increase the productivity, the mass ratio of the gel agent aqueous solution to the liquid phase is suitably at most equal to 50/50, more suitably equal to or less than 40/60, even more suitably equal to or less than 35/65, and most suitably equal to or less than 30/70. In view of these considerations, the mass ratio of the gel agent aqueous solution to the liquid phase (gel agent aqueous solution/liquid phase) is suitably in the range of 1/99-50/50, more suitably in the range of 3/97-40/60, even more suitably in the range of 4/96-35/65, and most suitably in the range of 5/95-30/70.

The temperature of the liquid phase when the gel agent aqueous solution is put thereto, which is equal to or lower than the gel point, is suitably at least equal to 0° C., more suitably equal to or higher than 5° C., even more suitably equal to or higher than 10° C., and still more suitably equal to or higher than 15° C., considering its aptitude for manufacturing. Meanwhile, from the same point of view, the temperature of the liquid phase is suitably at most equal to 60° C., more suitably equal to or lower than 50° C., even more suitably equal to or lower than 40° C., and still more suitably equal to or lower than 30° C. The temperature of the liquid phase is suitably in the range of 0-60° C., more suitably in the range of 5-50° C., even more suitably in the range of 10-40° C., still more suitably in the range of 10-30° C., and yet more suitably in the range of 15-30° C. To rapidly cool and solidify the gel agent aqueous solution and to achieve a high residual ratio by reducing the dissipation of dispersed particles into the liquid phase when the gel agent aqueous solution includes the dispersed particles, the temperature of the liquid phase is suitably lower than the gel point by at least 10° C., more suitably by not less than 20° C., and even more suitably by not less than 30° C.

To achieve a high residual ratio by reducing the dissipation of dispersed particles into the liquid phase when the gel agent aqueous solution includes the dispersed particles, the viscosity of the liquid phase at 20° C. is suitably at least equal to 1 mPa·s, more suitably equal to or greater than 100 mPa·s, even more suitably equal to or greater than 5000 mPa·s, still more suitably equal to or greater than 10000 mPa·s, and particularly suitably equal to or greater than 25000 mPa·s. Meanwhile, considering its aptitude for manufacturing, the viscosity of the liquid phase at 20° C. is suitably at most equal to 300000 mPa·s, more suitably equal to or less than 100000 mPa·s, even more suitably equal to or less than 70000 mPa·s, and particularly suitably equal to or less than 40000 mPa·s. In view of these considerations, the viscosity of the liquid phase is suitably in the range of 1-300000 mPa·s, more suitably in the range of 100-100000 mPa·s, even more suitably in the range of 5000-70000 mPa·s, yet more suitably in the range of 10000-40000 mPa·s, and particularly suitably in the range of 25000-40000 mPa·s. The viscosity of the liquid phase may be measured with a Type B viscometer.

Particularly when the liquid phase is an aqueous phase, dispersed particles will easily dissipate from the gel agent aqueous solution of the aqueous component into the liquid phase of the aqueous component. However, the dispersed particles can be effectively prevented from dissipating by increasing the viscosity of the liquid phase. Thus, in that case, the liquid phase that is an aqueous phase suitably has its viscosity increased by adding a thickener to the liquid phase. Examples of such thickeners include guar gum, locust bean gum, quince seed gum, carrageenan, galactan, gum arabic, tragacanth gum, pectin, mannan, starch, xanthan gum, dextran, succinoglucan, curdlan, hyaluronic acid, gelatin, casein, albumin, collagen, shellac, methyl cellulose, ethyl cellulose, hydroxyethyl cellulose, hydroxypropyl cellulose, carboxymethyl cellulose, methyl hydroxypropyl cellulose, soluble starch, carboxymethyl starch, methyl starch, hydroxypropyl starch, alginic acid propylene glycol esters, alginates, polyvinyl alcohol, polyvinyl pyrrolidone, polyvinyl methyl ethers, carboxy vinyl polymers, sodium polyacrylate, acrylic acid/alkyl methacrylate copolymers, acrylic acid Na/acryloyldimethyl taurate Na copolymers, polyacrylamides, polyvinyl methacrylate, polyethylene oxide, ethylene oxide-propylene oxide block copolymers, polyglycol-polyamine condensates, polymethyl methacrylate fine particles, bentonite, laponite, fine powder silicon oxide, colloidal alumina, and veegum. As the thickener, it is recommended to use one, two, or more of these. It is more recommendable to use one, two or more selected from the group consisting of carboxyvinyl polymers, sodium polyacrylate, acrylic acid/alkyl methacrylate copolymers, acrylic acid Na/acryloyldimethyl taurate Na copolymers, and polyacrylamide. The content of the thickener in the liquid phase is a required amount to increase the viscosity of the liquid phase to a desired value, and is suitably at least equal to 0.01 mass %, more suitably equal to or greater than 0.1 mass %, and even more suitably equal to or greater than 0.3 mass %. Meanwhile, the content of the thickener is suitably at most equal to 10 mass %, more suitably equal to or less than 5 mass %, and still more suitably equal to or less than 1 mass %. The content of the thickener is suitably in the range of 0.01-10 mass %, more suitably in the range of 0.1-5 mass %, and even more suitably in the range of 0.3-1 mass %.

The gel agent aqueous solution may be put into the liquid phase either indirectly via a gas phase or directly. Of these two options, it is recommended to put the gel agent aqueous solution into the liquid phase via a gas phase in order to improve the productivity by accelerating cooling. In addition, the gel agent aqueous solution may be put into the liquid phase as a continuous fluid, or as a discontinuous fluid, or as drips. Of these three options, it is recommended to put the gel agent aqueous solution as a continuous fluid such that the gel agent aqueous solution is cooled in the liquid phase to form a lump of a solidified product, in order to improve the productivity. Furthermore, when the gel agent aqueous solution is put into the liquid phase, the liquid phase may be cooled with a heat exchanger, for example, in order to cool the gel agent aqueous solution efficiently.

It is recommended to stir up the liquid phase, into which the gel agent aqueous solution has been put, in order to cool the gel agent aqueous solution efficiently. The liquid phase is suitably stirred up while the gel agent aqueous solution is being put and/or after the gel agent aqueous solution has been put. Furthermore, the liquid phase more suitably starts to be stirred up even before the gel agent aqueous solution is put thereto, and is more suitably stirred up continuously just after the gel agent aqueous solution has started to be put, while the gel agent aqueous solution is being put, and even after the gel agent aqueous solution has been put.

To cool the gel agent aqueous solution efficiently, the stirring energy to be applied while the liquid phase is being stirred up is suitably at least equal to 0.1 kW×second/m$^3$, more suitably equal to or greater than 100 kW×second/m$^3$, even more suitably equal to or greater than 500 kW×second/m$^3$, and particularly suitably equal to or greater than 800 kW×second/m$^3$. Furthermore, to achieve a high residual ratio by preventing the dispersed particles from dissipating into the liquid phase when the gel agent aqueous solution includes the dispersed particles, the stirring energy is suitably at most equal to 30000 kW×second/m$^3$, more suitably equal to or less than 15000 kW×second/m$^3$, even more suitably 10000 kW×second/m$^3$, still more suitably equal to or less than 8000 kW×second/m$^3$, yet more suitably equal to or less than 5000 kW×second/m$^3$, and particularly suitably 3000 kW×second/m$^3$. In view of these considerations, the stirring energy is suitably in the range of 0.1-30000 kW×second/m$^3$, more suitably in the range of 100-15000 kW×second/m$^3$, even more suitably in the range of 500-10000 kW×second/m$^3$, still more suitably in the range of 500-8000 kW×second/m$^3$, yet more suitably in the range of 500-5000 kW×second/m$^3$, and particularly suitably in the range of 800-3000 kW×second/m$^3$.

As used herein, the "stirring energy" is calculated by the specific equation described in Japanese Unexamined Patent Publication No. 2007-161683. For example, when a homomixer is used, the stirring energy may be calculated by the following Equation (I):

Stirring Energy (kW×second/m$^3$)=[Stirring Power $P$ (kW)]/[Process Liquid's Volume $V$ (m$^3$)]×Stirring Time (seconds)  (I)

In this Equation (I), the stirring power P (kW) is calculated by the following Experimental Equation 1:

Stirring Power $P$(kW)=$Np \times n^3 \times d^5 \times \rho$/1000 (Experimental Equation 1)

where Np indicates the number of powers (e.g., Np=1.5 in a homomixer with a stirring tank capacity of less than 10 L and Np=1.3 in a homomixer with a stirring tank capacity of equal to or greater than 10 L);
n indicates the stirring rotational frequency (−/second);
d indicates the diameter (m) of the impeller; and
ρ indicates the density (kg/m$^3$) of the process liquid.

A dispersant may be added to the liquid phase. Just as the dispersants enumerated above as being added to the gel agent aqueous solution that is a dispersion to distribute the dispersed particles, examples of the dispersants also include polymer emulsifying and dispersing agents, anionic surfactants, cationic surfactants, nonionic surfactants, and amphoteric surfactants. The same group of materials as those described above may be enumerated as specific dispersants. As the dispersant, it is recommended to use one, two, or more of these. Optionally, the dispersant added to the liquid phase may also function as a thickener. The content of the dispersant in the liquid phase is suitably at least equal to 0.001 mass %, more suitably equal to or greater than 0.01 mass %, and even more suitably equal to or greater than 0.1 mass %. Meanwhile, the content of the dispersant in the liquid phase is suitably at most equal to 10 mass %, more suitably equal to or less than 5 mass %, and even more suitably equal to or less than 1 mass %. The content of the dispersant in the liquid phase is suitably in the range of 0.001-10 mass %, more suitably in the range of 0.01-5 mass %, and even more suitably in the range of 0.1-1 mass %.

A cosmetic component may be added to, and contained in, the liquid phase before the gel agent aqueous solution is put into the liquid phase and/or after the gel agent aqueous solution has been put into the liquid phase. Adding a cosmetic component to the liquid phase in this manner allows for producing a cosmetic product while producing hydrogel particles by crushing a solidified product obtained by solidifying the gel agent aqueous solution contained in the liquid phase. That is to say, the method for producing hydrogel particles according to this embodiment can be incorporated into the method for producing a cosmetic product.

The cosmetic component may be added in advance to the liquid phase to which the gel agent aqueous solution has not been put yet. In that case, the liquid phase is suitably an emulsified liquid including the cosmetic component as emulsifying particles in order to improve the productivity of the cosmetic product. The liquid phase serving as such an emulsified liquid may be obtained by stirring up and emulsifying the liquid phase including the cosmetic component as an additive such that the cosmetic component will be emulsifying particles.

The cosmetic component may be added to the liquid phase to which the gel agent aqueous solution has already been put. In that case, the cosmetic component may be added in advance to the liquid phase to which the gel agent aqueous solution has not been put yet, and then the same or different cosmetic component may be further added to the liquid phase to which the gel agent aqueous solution has already been added. Optionally, the cosmetic component may be added to the liquid phase to which the gel agent aqueous solution has already been put either before the solidified product is crushed or after the solidified product has been crushed. Alternatively, the same or different cosmetic components may be added to the liquid phase both before and after the solidified product is crushed.

Examples of such cosmetic components include: polyether-modified silicones; cosmetic oils; humectants; intercellular lipids such as ceramides; ultraviolet absorbents such as titanium oxide, zinc oxide, and extracts of animals and plants; vitamins such as fat-soluble vitamins and water-soluble vitamins; chelating agents; pH adjusting agents; antiseptic agents; dyes; perfumes; medicinal components such as whitening, analgesics, anti-inflammatory agents, antipruritic agents, disinfectants, astringents, emollients, and hormonal agents; emulsifying agents; cleaning agents; and antioxidants. As the cosmetic component, it is recommended to use one, two, or more of these.

Examples of methods for crushing the solidified product (non-crosslinked hydrogel) obtained by solidifying the gel agent aqueous solution include: transmitting a liquid phase including the solidified product through a sieve such as a wire mesh, constituting a solidified product crushing means, in a state where the solidified product is contained in the liquid phase; shearing the liquid phase including the solidified product with a dispersing machine such as a line mixer, a disperser, a homogenizer, a milder, or a homomixer, in a state where the solidified product is contained in the liquid phase; and mechanically crushing the solidified product in a state where the solidified product has already been separated from the liquid phase.

From the standpoint of producing hydrogel particles inexpensively and simply, the solidified product is suitably crushed by allowing a liquid phase including the solidified product, among other things, to be transmitted through a sieve (serving as an exemplary solidified product crushing member). Specifically, using an apparatus including a pipe and a sieve provided halfway through the pipe, a solidified product, obtained by cooling and solidifying a gel agent aqueous solution forming a non-crosslinked hydrogel, may be allowed to flow through the pipe and then a liquid phase including the solidified product may be transmitted through the sieve to crush the solidified product.

The aperture of the sieve is appropriately selected according to the required particle size of the hydrogel particles. Considering that a product such as a cosmetic product, including the hydrogel particles thus obtained, will feel soft in use, the aperture of the sieve is suitably at least equal to 1 μm, more suitably equal to or greater than 10 μm, and even more suitably equal to or greater than 50 μm. Meanwhile, the aperture of the sieve is suitably at most equal to 1000 μm, more suitably equal to or less than 800 μm, and even more suitably equal to or less than 300 μm. The aperture of the sieve is suitably in the range of 1-1000 μm, more suitably in the range of 10-800 μm, and even more suitably in the range of 50-300 μm.

If the solidified product is crushed by transmitting the liquid phase including the solidified product through a sieve, the liquid phase including the solidified product is suitably transmitted through the sieve a number of times in order to reduce a variation in the particle size of the resultant hydrogel particles. In this case, the liquid phase including the solidified product may be cyclically transmitted through either the same sieve or multiple different sieves a number of times. Alternatively, the liquid phase including the solidified product may also be transmitted through a plurality of sieves which are arranged in series either continuously or at intervals.

Considering that a product such as a cosmetic product, including the hydrogel particles thus obtained, will feel soft in use, if the liquid phase including the solidified product is transmitted through a plurality of sieves, the number of the sieves to use is suitably at least equal to two, and more suitably equal to or greater than three. Meanwhile, considering its productivity and cost effectiveness, the number of the sieves to use is suitably at most equal to ten, and more suitably equal to or less than five. In view of these considerations, the number of the sieves to use is suitably in the range of two to ten, and more suitably in the range of three to five. Those sieves may have either the same aperture or mutually different apertures. Alternatively, some of those sieves may have the same aperture and the other sieves may have different apertures.

If the plurality of sieves includes sieves with mutually different apertures, then the plurality of sieves are suitably arranged in the descending order of their apertures such that one of the sieves having the largest aperture is arranged more upstream of any other one of the sieves. In that case, in each adjacent pair of the sieves having mutually different apertures, among those sieves arranged in the descending order of their apertures such that the sieve having the largest aperture is arranged most upstream, the ratio of the aperture of the downstream one of the pair to that of the other, upstream one is suitably at least equal to 1%, more suitably equal to or greater than 10%, even more suitably equal to or greater than 20%, and is suitably at most equal to 100%, more suitably equal to or less than 90%, and even more suitably equal to or less than 80% from the standpoint of aptitude for manufacturing. In each adjacent pair of the sieves having mutually different apertures, among those sieves arranged in the descending order of their apertures such that the sieve having the largest aperture is arranged most upstream, the ratio of the aperture of the downstream one of the pair to that of the other, upstream one is suitably in the range of 1-100%, more suitably in the range of 10-90%, and even more suitably in the range of 20-80%. Also, among those sieves arranged in the descending order of their apertures such that the sieve having the largest aperture is arranged most upstream, the ratio of the aperture of the most downstream one of the sieves to the aperture of the most upstream sieve is suitably at least equal to 0.1%, more suitably equal to or greater than 1%, and even more suitably equal to or greater than 5%, and is suitably at most equal to 100%, more suitably equal to or less than 90%, and even more suitably equal to or less than 80% from the standpoint of aptitude for manufacturing. Among those sieves arranged in the descending order of their apertures such that the sieve having the largest aperture is arranged most upstream, the ratio of the aperture of the most downstream sieve to that of the most upstream sieve is suitably in the range of 0.1-100%, more suitably in the range of 1-90%, and even more suitably in the range of 5-80%.

The method for producing hydrogel particles according to the embodiment allows for obtaining hydrogel particles contained in a liquid phase.

In view of the solidifiability of the gel agent aqueous solution, the content of the gel agent in the liquid phase including hydrogel particles is suitably at least equal to 0.001 mass %, more suitably equal to or greater than 0.01 mass %, even more suitably equal to or greater than 0.05 mass %, still more suitably equal to or greater than 0.1 mass %, yet more suitably equal to or greater than 0.2 mass %, and particularly suitably equal to or greater than 0.3 mass %. Furthermore, considering that a product such as a cosmetic product, including the hydrogel particles thus obtained, will feel soft in use, the content of the gel agent in the liquid phase is suitably at most equal to 4 mass %, more suitably equal to or less than 2 mass %, and even more suitably equal to or less than 1 mass %. In view of these considerations, the content of the gel agent in the liquid phase including hydrogel particles is suitably in the range of 0.001-4 mass %, more suitably in the range of 0.01-2 mass %, even more suitably in the range of 0.05-1 mass %, still more suitably in the range of 0.1-1 mass %, yet more suitably in the range of 0.2-1 mass %, and most suitably in the range of 0.3-1 mass %.

To achieve the effect by the function of the dispersed particles, the content of the dispersed particles in the liquid phase including hydrogel particles is suitably at least equal to 0.01 mass %, more suitably equal to or greater than 0.5 mass %, even more suitably equal to or greater than 1 mass %, and particularly suitably equal to or greater than 5 mass %. Meanwhile, considering that a product such as a cosmetic product, including the hydrogel particles thus obtained, will feel soft in use, the content of the dispersed particles in the liquid phase including hydrogel particles is suitably at most equal to 30 mass %, more suitably equal to or less than 20 mass %, and even more suitably equal to or less than 10 mass %. In view of these considerations, the content of the dispersed particles in the liquid phase including hydrogel particles is suitably in the range of 0.01-30 mass %, more suitably in the range of 0.5-20 mass %, even more suitably in the range of 1-10 mass %, and yet more suitably in the range of 5-10 mass %.

To stabilize the dispersion and emulsion, the content of the dispersant and other additives in the hydrogel particles contained in the liquid phase is suitably at least equal to 0.001 mass %, more suitably equal to or greater than 0.005 mass %, and even more suitably equal to or greater than 0.01 mass %. Meanwhile, in view of safety considerations, the content of the dispersant and other additives in the hydrogel particles is suitably at most equal to 0.5 mass %, more suitably equal to or less than 0.3 mass %, and even more suitably equal to or less than 0.2 mass %. In view of these considerations, the content of the dispersant and other additives in the hydrogel particles contained in the liquid phase is suitably in the range of 0.001-0.5 mass %, more suitably in the range of 0.005-0.3 mass %, and even more suitably in the range of 0.01-0.2 mass %.

Considering that a product such as a cosmetic product, including the hydrogel particles thus obtained, will feel soft in use, the content of the thickener in the liquid phase including hydrogel particles is suitably at least equal to 0.05 mass %, more suitably equal to or greater than 0.1 mass %, and even more suitably equal to or greater than 0.4 mass %. Meanwhile, considering that a product such as a cosmetic product, including the hydrogel particles thus obtained, will feel soft in use, the content of the thickener in the liquid phase including hydrogel particles is suitably at most equal to 5 mass %, more suitably equal to or less than 3 mass %, even more suitably equal to or less than 1.5 mass %, and yet more suitably equal to or less than 0.8 mass %. In view of these considerations, the content of the thickener in the liquid phase including hydrogel particles is suitably in the range of 0.05-5 mass %, more suitably in the range of 0.1-3 mass %, even more suitably in the range of 0.4-1.5 mass %, and yet more suitably in the range of 0.4-0.8 mass %.

The hydrogel particles obtained to be contained in the liquid phase may be separated from inside the liquid phase and added to a cosmetic product, for example. Alternatively, a cosmetic component or any other component may be added to the liquid phase including the hydrogel particles to obtain a cosmetic product or any other product as described above. In this case, the liquid phase may include components which can be contained in the hydrogel particles.

Considering that a product such as a cosmetic product, including the hydrogel particles thus obtained, will feel soft in use, the particle shape of the hydrogel particles obtained by the method according to the embodiment is suitably indefinite as shown in FIG. 1 and is suitably non-uniform.

Considering that a product such as a cosmetic product, including the hydrogel particles thus obtained, will feel soft in use, the volume mean particle size of the hydrogel particles is suitably at least equal to 0.1 μm, more suitably equal to or greater than 10 μm, and even more suitably equal to or greater than 20 μm. Meanwhile, the volume mean particle size of the hydrogel particles is suitably at most equal to 10000 μm, more suitably equal to or less than 1000 μm, and even more suitably equal to or less than 250 μm. The volume mean particle size of the hydrogel particles is suitably in the range of 0.1-10000 μm, more suitably in the range of 10-1000 μm, and even more suitably in the range of 20-250 μm. The volume mean particle size of the hydrogel particles may be measured by a laser diffraction/scattering method with a laser diffraction/scattering particle size analyzer (e.g., LA-920 manufactured by HORIBA, Ltd.) or a screening method. The laser diffraction/scattering method is suitably applied to the measurement of particles with a particle size of 1000 μm or less, while the screening method is suitably applied to the measurement of particles with a particle size of greater than 1000 μm.

Considering that a product such as a cosmetic product, including the hydrogel particles thus obtained, will feel soft to the skin, the aspect ratio of the hydrogel particles is suitably at least equal to 1.1, more suitably equal to or greater than 2, even more suitably equal to or greater than 3, and most suitably equal to or greater than 3.5. Meanwhile, considering that a product such as a cosmetic product, including the hydrogel particles thus obtained, will feel soft in use, the aspect ratio of the hydrogel particles is suitably at most equal to 20, more suitably equal to or less than 10, even more suitably equal to or less than 5, and most suitably equal to or less than 4. In view of these considerations, the aspect ratio of the hydrogel particles is suitably in the range of 1.1-20, more suitably in the range of 2.0-10, even more suitably in the range of 3.0-5.0, and most suitably in the range of 3.5-4.0. Here the "aspect ratio" refers to an "index representing the shape of a particle defined as "the ratio of the maximum major diameter to the width perpendicular to the maximum major diameter in a microscopic image of the particle" according to the JIS Z8900-1: 2008 standard. According to the present application, the "aspect ratio of hydrogel particles" is obtained by dividing, in microscopic images of arbitrarily selected 10 particles, the largest major diameter thereof by the width of its perpendicular bisector, and by calculating their average.

If the hydrogel particles include dispersed particles, the ratio of the dispersed particles remaining in the particles without dissipating into the liquid phase, i.e., the residual ratio, is suitably at least equal to 50%, more suitably equal to or greater than 80%, even more suitably equal to or greater than 90%, and most suitably equal to or greater than 100%. This residual ratio is obtained by the analysis method to be described later by way of examples.

Note that the method for producing hydrogel particles according to the embodiment described above may be carried out by any of a batch process, a semi-batch process, or a continuous process.

Regarding the embodiment described above, the following configurations are further disclosed herein:

<1> A method for producing hydrogel particles, the method comprising the steps of: solidifying an aqueous solution in which a gel agent forming a non-crosslinked hydrogel is dissolved and which has a gel point of 30° C. or more by introducing the aqueous solution into a liquid phase having a temperature of equal to or lower than the gel point; and crushing a solidified product obtained by solidifying the aqueous solution in which the gel agent is dissolved.

<2> The method of <1>, wherein crushing the solidified product includes crushing the solidified product contained in the liquid phase.

<3> The method of <2>, wherein crushing the solidified product is performed by transmitting, through a sieve, the liquid phase including the solidified product.

<4> The method of <3>, comprising transmitting the liquid phase including the solidified product through the sieve a number of times.

<5> The method of <4>, comprising transmitting the liquid phase including the solidified product through a plurality of sieves arranged in series.

<6> The method of <5>, wherein the number of the plurality of sieves is suitably at least equal to two, more suitably equal to or greater than three, and suitably at most equal to ten, more suitably equal to or less than five.

<7> The method of <5> or <6>, wherein the number of the plurality of sieves is suitably in the range of two to ten, and more suitably in the range of three to five.

<8> The method of any one of <5> to <7>, wherein the plurality of sieves includes sieves having mutually different apertures.

<9> The method of <8>, wherein arranging the plurality of sieves includes arranging the plurality of sieves in the descending order of their apertures such that one of the sieves having the largest aperture is arranged more upstream of any other one of the sieves.

<10> The method of <9>, wherein in each adjacent pair of the sieves having mutually different apertures, among the plurality of sieves arranged in the descending order of their apertures such that the sieve having the largest aperture is arranged more upstream of any other one of the sieves, the ratio of the aperture of the downstream one of the pair to the aperture of the upstream one of the pair is suitably at least equal to 1%, more suitably equal to or greater than 10%, even more suitably equal to or greater than 20%, and is suitably at most equal to 100%, more suitably equal to or less than 90%, and even more suitably equal to or less than 80%.

<11> The method of <9> or <10>, wherein in each adjacent pair of the sieves having mutually different apertures, among the plurality of sieves arranged in the descending order of their apertures such that the sieve having the largest aperture is arranged more upstream of any other one of the sieves, the ratio of the aperture of the downstream one of the pair to the aperture of the upstream one of the pair is suitably in the range of 1-100%, more suitably in the range of 10-90%, and even more suitably in the range of 20-80%.

<12> The method of any one of <9> to <11>, wherein among the plurality of sieves arranged in the descending order of their apertures such that the sieve having the largest aperture is arranged more upstream of any other one of the sieves, the ratio of the aperture of the most downstream one of the sieves to the aperture of the most upstream one of the sieves is suitably at least equal to 0.1%, more suitably equal to or greater than 1%, and even more suitably equal to or greater than 5%, and is suitably at most equal to 100%, more suitably equal to or less than 90%, and even more suitably equal to or less than 80%.

<13> The method of any one of <9> to <12>, wherein among the plurality of sieves arranged in the descending order of their apertures such that the sieve having the largest aperture is arranged more upstream of any other one of the sieves, the ratio of the aperture of the most downstream one of the sieves to the aperture of the most upstream one of the sieves is suitably in the range of 0.1-100%, more suitably in the range of 1-90%, and even more suitably in the range of 5-80%.

<14> The method of any one of <3> to <13>, wherein the aperture of the at least one sieve is suitably at least equal to 1 μm, more suitably equal to or greater than 10 μm, and even more suitably equal to or greater than 50 μm, and is suitably at most equal to 1000 μm, more suitably equal to or less than 800 μm, and even more suitably equal to or less than 300 μm.

<15> The method of any one of <3> to <14>, wherein the aperture of the at least one sieve is suitably in the range of 1-1000 μm, more suitably in the range of 10-800 μm, and even more suitably in the range of 50-300 μm.

<16> The method of any one of <1> to <15>, comprising stirring up the liquid phase into which the aqueous solution, in which the gel agent is dissolved, has been put.

<17> The method of <16>, wherein stirring up the liquid phase includes stirring up the liquid phase while the gel agent aqueous solution is being put into the liquid phase and/or after the gel agent aqueous solution has been put into the liquid phase.

<18> The method of <17>, wherein stirring up the liquid phase includes starting stirring up the liquid phase before putting the gel agent aqueous solution into the liquid phase.

<19> The method of any one of <16> to <18>, wherein stirring energy to be applied while the liquid phase is being stirred up is suitably at least equal to 0.1 kW×second/m$^3$, more suitably equal to or greater than 100 kW×second/m$^3$, even more suitably equal to or greater than 500 kW×second/m$^3$, and particularly suitably equal to or greater than 800 kW×second/m$^3$, and is suitably at most equal to 30000 kW×second/m$^3$, more suitably equal to or less than 15000 kW×second/m$^3$, even more suitably 10000 kW×second/m$^3$, still more suitably equal to or less than 8000 kW×second/m$^3$, yet more suitably equal to or less than 5000 kW×second/m$^3$, and particularly suitably equal to or less than 3000 kW×second/m$^3$.

<20> The method of any one of <16> to <19>, wherein the stirring energy to be applied while the liquid phase is being stirred up is suitably in the range of 0.1-30000 kW×second/m$^3$, more suitably in the range of 100-15000 kW×second/m$^3$, even more suitably in the range of 500-10000 kW×second/m$^3$, still more suitably in the range of 500-8000 kW×second/m$^3$, yet more suitably in the range of 500-5000 kW×second/m³, and particularly suitably in the range of 800-3000 kW×second/m³.

<21> The method of any one of <1> to <20>, comprising putting, as a continuous fluid, the gel agent aqueous solution into the liquid phase.

<22> The method of any one of <1> to <21>, comprising putting the aqueous solution in which the gel agent is dissolved into the liquid phase via a gas phase.

<23> The method of any one of <1> to <22>, wherein the viscosity of the liquid phase at 20° C. is suitably at least equal to 1 mPa·s, more suitably equal to or greater than 100 mPa·s, even more suitably equal to or greater than 5000 mPa·s, still more suitably equal to or greater than 10000 mPa·s, and particularly suitably equal to or greater than 25000 mPa·s, and is suitably at most equal to 300000 mPa·s, more suitably equal to or less than 100000 mPa·s, even more suitably equal to or less than 70000 mPa·s, and particularly suitably equal to or less than 40000 mPa·s.

<24> The method of any one of <1> to <23>, wherein the viscosity of the liquid phase at 20° C. is suitably in the range of 1-300000 mPa·s, more suitably in the range of 100-100000 mPa·s, even more suitably in the range of 5000-70000 mPa·s, yet more suitably in the range of 10000-40000 mPa·s, and most suitably in the range of 25000-40000 mPa·s.

<25> The method of any one of <1> to <24>, wherein the liquid phase is an aqueous phase.

<26> The method of <25>, wherein the liquid phase contains a thickener.

<27> The method of <26>, wherein the thickener is one, two, or more selected from the group consisting of guar gum, locust bean gum, quince seed gum, carrageenan, galactan, gum arabic, tragacanth gum, pectin, mannan, starch, xanthan gum, dextran, succinoglucan, curdlan, hyaluronic acid, gelatin, casein, albumin, collagen, shellac, methyl cellulose, ethyl cellulose, hydroxyethyl cellulose, hydroxypropyl cellulose, carboxymethyl cellulose, methyl hydroxypropyl cellulose, soluble starch, carboxymethyl starch, methyl starch, hydroxypropyl starch, alginic acid propylene glycol esters, alginates, polyvinyl alcohol, polyvinyl pyrrolidone, polyvinyl methyl ethers, carboxy vinyl polymers, sodium polyacrylate, acrylic acid/alkyl methacrylate copolymers, polyvinyl methacrylate, polyethylene oxide, ethylene oxide-propylene oxide block copolymers, polyglycol-polyamine condensates, polymethyl methacrylate fine particles, bentonite, laponite, fine powder silicon oxide, colloidal alumina, and veegum.

<28> The method of <26> or <27>, wherein the content of the thickener in the liquid phase is suitably at least equal to 0.01 mass %, more suitably equal to or greater than 0.1 mass %, and even more suitably equal to or greater than 0.3 mass %, and is suitably at most equal to 10 mass %, more suitably equal to or less than 5 mass %, and still more suitably equal to or less than 1 mass %.

<29> The method of any one of <26> to <28>, wherein the content of the thickener in the liquid phase is suitably in the range of 0.01-10 mass %, more suitably in the range of 0.1-5 mass %, and even more suitably in the range of 0.3-1 mass %.

<30> The method of any one of <26> to <29>, wherein the content of the thickener in the liquid phase including the hydrogel particles is suitably at least equal to 0.05 mass %, more suitably equal to or greater than 0.1 mass %, and even more suitably equal to or greater than 0.4 mass %, and is suitably at most equal to 5 mass %, more suitably equal to or less than 3 mass %, even more suitably equal to or less than 1.5 mass %, and yet more suitably equal to or less than 0.8 mass %.

<31> The method of any one of <26> to <30>, wherein the content of the thickener in the liquid phase including the hydrogel particles is suitably in the range of 0.05-5 mass %, more suitably in the range of 0.1-3 mass %, even more suitably in the range of 0.4-1.5 mass %, and yet more suitably in the range of 0.4-0.8 mass %.

<32> The method of any one of <1> to <31>, wherein the aqueous solution in which the gel agent is dissolved is a dispersion in which dispersed particles are distributed.

<33> The method of <32>, wherein the dispersed particles are one, two, or more selected from the group consisting of oil components, water-insoluble complexes including catechins, and powders for cosmetic products.

<34> The method of <32> or <33>, wherein the content of the dispersed particles in the liquid phase including hydrogel particles is suitably at least equal to 0.01 mass %, more suitably equal to or greater than 0.5 mass %, even more suitably equal to or greater than 1 mass %, and particularly suitably equal to or greater than 5 mass %, and is suitably at most equal to 30 mass %, more suitably equal to or less than 20 mass %, and even more suitably equal to or less than 10 mass %.

<35> The method of any one of <32> to <34>, wherein the content of the dispersed particles in the liquid phase including the hydrogel particles is suitably in the range of 0.01-30 mass %, more suitably in the range of 0.5-20 mass %, even more suitably in the range of 1-10 mass %, and yet more suitably in the range of 5-10 mass %.

<36> The method of any one of <32> to <35>, wherein the aqueous solution in which the gel agent is dissolved contains at least one of a dispersant or an emulsifier.

<37> The method of <36>, wherein at least one of the dispersant or the emulsifier includes one, two, or more selected from the group consisting of polymer emulsifying and dispersing agents, anionic surfactants, cationic surfactants, nonionic surfactants, and amphoteric surfactants.

<38> The method of <36> or <37>, wherein the content of at least one of the dispersant or the emulsifier in the aqueous solution in which the gel agent is dissolved is suitably at least equal to 0.01 mass %, more suitably equal to or greater than 0.05 mass %, and even more suitably equal to or greater than 0.1 mass %, and is suitably at most equal to 5 mass %, more suitably equal to or less than 3 mass %, and even more suitably equal to or less than 1 mass %.

<39> The method of any one of <36> to <38>, wherein the content of at least one of the dispersant or the emulsifier in the aqueous solution in which the gel agent is dissolved is suitably in the range of 0.01-5 mass %, more suitably in the range of 0.05-3 mass %, and even more suitably in the range of 0.1-1 mass %.

<40> The method of any one of <36> to <39>, wherein the content of at least one of the dispersant or the emulsifier in the hydrogel particles contained in the liquid phase is suitably at least equal to 0.001 mass %, more suitably equal to or greater than 0.005 mass %, and even more suitably equal to or greater than 0.01 mass %, and is suitably at most equal to 0.5 mass %, more suitably equal to or less than 0.3 mass %, and even more suitably equal to or less than 0.2 mass %.

<41> The method of any one of <36> to <40>, wherein the content of at least one of the dispersant or the emulsifier in the hydrogel particles contained in the liquid phase is suitably in the range of 0.001-0.5 mass %, more suitably in the range of 0.005-0.3 mass %, and even more suitably in the range of 0.01-0.2 mass %.

<42> The method of any one of <32> to <41>, wherein the residual ratio of the hydrogel particles is suitably at least equal to 50%, more suitably equal to or greater than 80%, even more suitably equal to or greater than 90%, and most suitably 100%.

<43> The method of any one of <1> to <42>, wherein the mass ratio of the aqueous solution in which the gel agent is dissolved to the liquid phase (gel agent aqueous solution/liquid phase) is suitably at least equal to 1/99, more suitably equal to or greater than 3/97, even more suitably equal to or greater than 4/96, and particularly suitably equal to or greater than 5/95, and is suitably at most equal to 50/50, more suitably equal to or less than 40/60, even more suitably equal to or less than 35/65, and particularly suitably equal to or less than 30/70.

<44> The method of any one of <I> to <43>, wherein the mass ratio of the aqueous solution in which the gel agent is dissolved to the liquid phase (gel agent aqueous solution/liquid phase) is suitably in the range of 1/99-50/50, more suitably in the range of 3/97-40/60, even more suitably in the range of 4/96-35/65, and most suitably in the range of 5/95-30/70.

<45> The method of any one of <1> to <44>, wherein the aspect ratio of the hydrogel particles is suitably at least equal to 1.1, more suitably equal to or greater than 2, even more suitably equal to or greater than 3, and most suitably equal to or greater than 3.5, and is suitably at most equal to 20, more suitably equal to or less than 10, even more suitably equal to or less than 5, and most suitably equal to or less than 4.

<46> The method of any one of <1> to <45>, wherein the aspect ratio of the hydrogel particles is suitably in the range of 1.1-20, more suitably in the range of 2.0-10, even more suitably in the range of 3.0-5.0, and most suitably in the range of 3.5-4.0.

<47> The method of any one of <1> to <46>, wherein the hydrogel particles have indefinite particle shapes.

<48> The method of any one of <1> to <47>, wherein the hydrogel particles have non-uniform particle shapes.

<49> The method of any one of <1> to <48>, wherein the volume mean particle size of the hydrogel particles is suitably at least equal to 0.1 μm, more suitably equal to or greater than 10 μm, and even more suitably equal to or greater than 20 and is suitably at most equal to 10000 μm, more suitably equal to or less than 1000 μm, and even more suitably equal to or less than 250 μm.

<50> The method of any one of <1> to <49>, wherein the volume mean particle size of the hydrogel particles is suitably in the range of 0.1-10000 μm, more suitably in the range of 10-1000 μm, and even more suitably in the range of 20-250 μm.

<51> The method of any one of <1> to <50>, wherein the gel agent is one, two, or more selected from the group consisting of agar, carrageenan, gellan gum, xanthan gum, and high methoxyl pectin.

<52> The method of <51>, wherein the gel agent is agar.

<53> The method of <52>, wherein the temperature of the gel agent aqueous solution is equal to or higher than the melting temperature of the gel agent and equal to or lower than the boiling point of water, and is suitably in the range of 75-100° C., and more suitably in the range of 80-100° C.

<54> The method of any one of <1> to <53>, wherein the gel point of the gel agent aqueous solution is suitably at most equal to 50° C. and more suitably equal to or lower than 45° C.

<55> The method of any one of <1> to <54>, wherein the content of the gel agent in the gel agent aqueous solution is suitably at least equal to 0.1 mass %, more suitably equal to or greater than 0.3 mass %, even more suitably equal to or greater than 0.4 mass %, and yet more suitably equal to or greater than 0.5 mass %, and is suitably at most equal to 8.0 mass %, more suitably equal to or less than 7.0 mass %, even more suitably equal to or less than 6.0 mass %, yet more suitably equal to or less than 5.0 mass %, and particularly suitably equal to or less than 3.0 mass %.

<56> The method of any one of <1> to <55>, wherein the content of the gel agent in the gel agent aqueous solution is suitably in the range of 0.1-8 mass %, more suitably in the range of 0.3-7 mass %, even more suitably in the range of 0.4-6 mass %, yet more suitably in the range of 0.5-5 mass %, and particularly suitably in the range of 0.5-3 mass %.

<57> The method of any one of <1> to <56>, wherein the content of the gel agent in the liquid phase including the hydrogel particles is suitably at least equal to 0.001 mass %, more suitably equal to or greater than 0.01 mass %, even more suitably equal to or greater than 0.05 mass %, still more suitably equal to or greater than 0.1 mass %, yet more suitably equal to or greater than 0.2 mass %, and particularly suitably equal to or greater than 0.3 mass %, and is suitably at most equal to 4 mass %, more suitably equal to or less than 2 mass %, and even more suitably equal to or less than 1 mass %.

<58> The method of any one of <1> to <57>, wherein the content of the gel agent in the liquid phase including hydrogel particles is suitably in the range of 0.001-4 mass %, more suitably in the range of 0.01-2 mass %, even more suitably in the range of 0.05-1 mass %, still more suitably in the range of 0.1-1 mass %, yet more suitably in the range of 0.2-1 mass %, and most suitably in the range of 0.3-1 mass %.

<59> The method of any one of <1> to <58>, wherein the temperature of the liquid phase is suitably at least equal to 0° C., more suitably equal to or higher than 5° C., even more suitably equal to or higher than 10° C., and still more suitably equal to or higher than 15° C., and is suitably at most equal to 60° C., more suitably equal to or lower than 50° C., even more suitably equal to or lower than 40° C., and still more suitably equal to or lower than 30° C.

<60> The method of any one of <1> to <59>, wherein the temperature of the liquid phase is suitably in the range of 0-60° C., more suitably in the range of 5-50° C., even more suitably in the range of 10-40° C., still more suitably in the range of 10-30° C., and yet more suitably in the range of 15-30° C.

<61> The method of any one of <1> to <60>, wherein the temperature of the liquid phase is suitably lower than the gel point by at least 10° C., more suitably by not less than 20° C., and even more suitably by not less than 30° C.

<62> The method of any one of <1> to <61>, wherein the gel agent aqueous solution is directly injected into the liquid phase.

<63> The method of any one of <1> to <62>, wherein the liquid phase is cooled when the gel agent aqueous solution is put into the liquid phase.

<64> A method for producing a cosmetic product, the method comprising the steps of: solidifying an aqueous solution in which a gel agent forming a non-crosslinked hydrogel is dissolved and which has a gel point of 30° C. or more by putting the aqueous solution into a liquid phase having a temperature of equal to or lower than the gel point; and crushing a solidified product included in the liquid phase and obtained by solidifying the aqueous solution in which the gel agent is dissolved.

<65> The method of <64>, comprising adding a cosmetic component in advance to the liquid phase into which the aqueous solution in which the gel agent is dissolved is yet to be put.

<66> The method of <65>, wherein the liquid phase is an emulsified liquid including the cosmetic component as emulsifying particles.

<67> The method of any one of <64> to <66>, comprising adding a cosmetic component to the liquid phase into which the aqueous solution in which the gel agent is dissolved has been put.

<68> The method of <67>, comprising adding the cosmetic component to the liquid phase after the solidified product has been crushed.

<69> An apparatus for producing hydrogel particles of a non-crosslinked hydrogel or a cosmetic product including the hydrogel particles, the apparatus comprising: a pipe configured to allow a liquid phase, including a solidified product obtained by cooling and solidifying an aqueous solution in which a gel agent, forming the non-crosslinked hydrogel, is dissolved, to flow therethrough; and a solidified product crushing member provided halfway through the pipe.

<70> The apparatus of <69>, wherein the solidified product crushing member is configured as a sieve.

<71> The apparatus of <70>, wherein the sieve configured as the solidified product crushing member includes a plurality of sieves.

<72> The apparatus of <70> or <71>, wherein the aperture of the sieve constituting the solidified product crushing member is suitably at least equal to 1 µm, more suitably equal to or greater than 10 µm, and even more suitably equal to or greater than 50 µm, and is suitably at most equal to 1000 µm, more suitably equal to or less than 800 µm, and even more suitably equal to or less than 300 µm.

<73> The apparatus of any one of <70> to <72>, wherein the aperture of the sieve constituting the solidified product crushing member is suitably in the range of 1-1000 µm, more suitably in the range of 10-800 µm, and even more suitably in the range of 50-300 µm.

EXAMPLES

Figure 2:
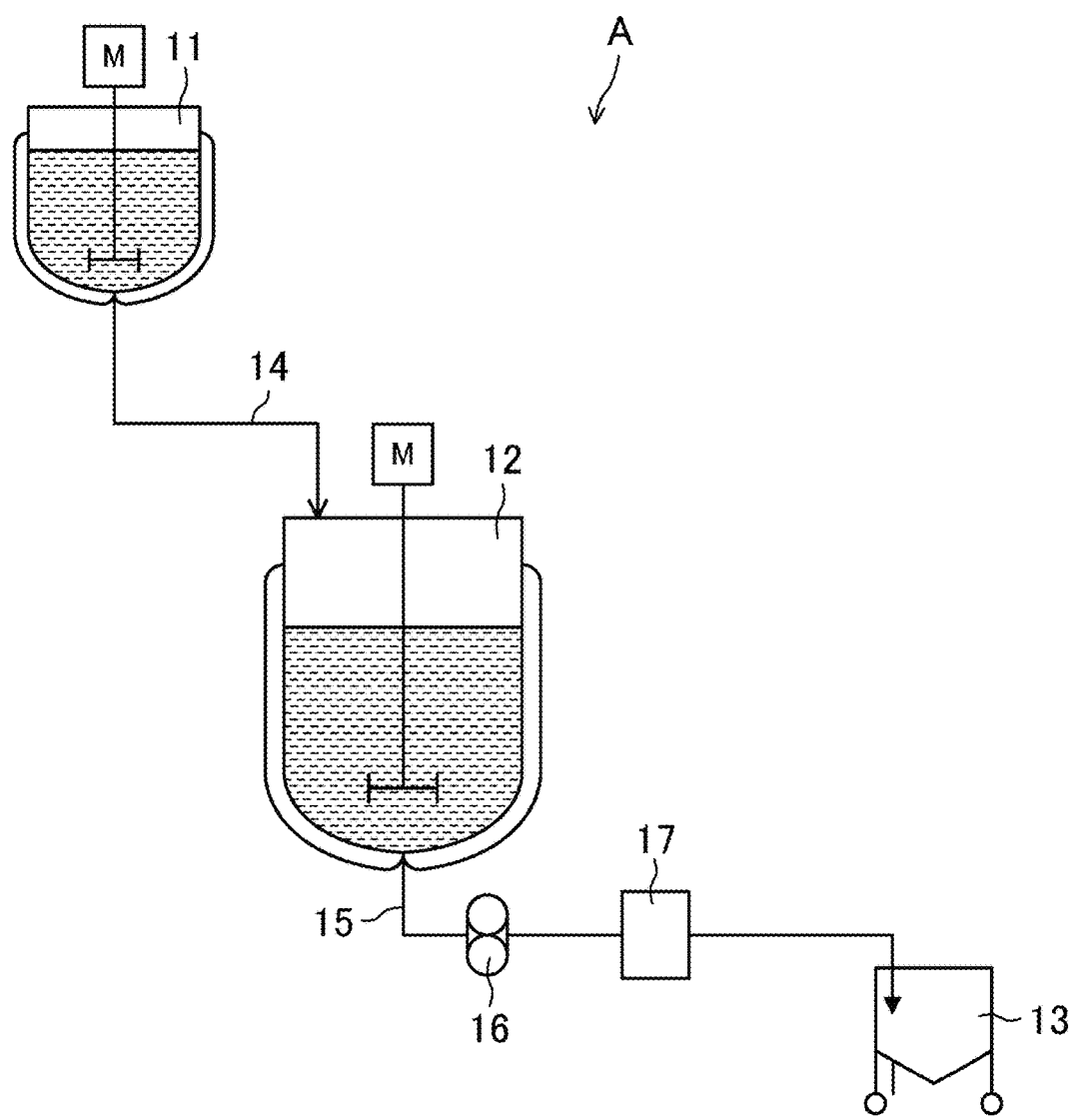
FIG. 2 Illustrates a configuration for an apparatus for use to produce hydrogel particles and a cosmetic product in first to fourth examples.

FIG. 2 illustrates an apparatus A that was used to produce hydrogel particles and cosmetic products in the following first to fourth examples.

This apparatus A includes an emulsifying tank 11, a blending tank 12, and a collection tank 13, each having a stirring mechanism. A feed pipe 14 extends from the emulsifying tank 11 to the blending tank 12, and a discharge pipe 15 extends from the blending tank 12 to the collection tank 13. A pump 16 is provided halfway through the discharge pipe 15, and a sieve 17 is arranged downstream of the pump 16 and has an aperture of 100 µm.

First Example

Hydrogel particles representing the following Examples 1-1 to 1-11 were produced with the apparatus A shown in FIG. 2. The specifics of those examples are also shown in Tables 1-1 to 1-3.

Example 1-1

A dispersed particle component liquid of an oil component, including monoglyceride stearate (RHEODOL MS-60 manufactured by Kao Corporation) as a solid fat and diethylamino hydroxybenzoyl hexyl benzoate (Uvinul A plus manufactured by BASF Japan Ltd.) as a crystalline organic ultraviolet absorbent, was prepared. In this case, these components were blended together so that the resultant hydrogel particles would include 13.5 mass % of monoglyceride stearate and 13.5 mass % of diethylamino hydroxybenzoyl hexyl benzoate.

Meanwhile, a hydrogel component aqueous solution, including agar as a gel agent (UP-16 manufactured by Ina Food Industry Co., Ltd.), an acrylic acid-alkyl methacrylate copolymer (PEMULEN TR-2 manufactured by Nikko Chemicals Co., Ltd.) and polyvinyl alcohol (GOHSENOL EG-05 manufactured by Nippon Synthetic Chemical Industry Co., Ltd.) as dispersants, a 1N NaOH aqueous solution (manufactured by Kishida Chemical Co., Ltd.) as a pH adjusting agent and ion-exchanged water, was also prepared. In this case, these components were blended together so that the resultant hydrogel particles would include 2.0 mass % of agar, 0.1 mass % of acrylic acid-alkyl methacrylate copolymer, 0.5 mass % of polyvinyl alcohol, 0.75 mass % of 1N NaOH aqueous solution, and the ion-exchanged water and other substances as the balance.

Then, the dispersed particle component liquid and the hydrogel component aqueous solution were prepared to have a total weight of 1000 g and a mass ratio of 27:73, and then dissolved under heat at 80° C. and 90° C., respectively. In this state, in the emulsifying tank 11 of the apparatus A, the dispersed particle component liquid was added to the hydrogel component aqueous solution. Then, the resultant mixture was stirred up for 1 minute at a rotational frequency of 8000 rpm with a homomixer (T. K. Robomix manufactured by PRIMIX Corporation), thereby preparing a gel agent aqueous solution as an oil-in-water dispersion. This gel agent aqueous solution had the volume mean particle size of its dispersed particles measured by a laser diffraction/scattering method with a laser diffraction/scattering particle size analyzer (LA-920 manufactured by HORIBA, Ltd.). As a result, the mean particle size was 5 µm. Also, the gel point of this gel agent aqueous solution was measured to be 30° C. or more.

Meanwhile, in the blending tank 12, an acrylic acid-alkyl methacrylate copolymer (PEMULEN TR-2 manufactured by Nikko Chemicals Co., Ltd.) was added as a thickener to, and dissolved in, the ion-exchanged water. Thereafter, the mixture was neutralized with the addition of a 48 mass % KOH aqueous solution (manufactured by Kishida Chemical Co., Ltd.) to prepare 2333 g of a liquid phase. The liquid phase included 0.79 mass % of acrylic acid-alkyl methacrylate copolymer, 0.31 mass % of 48 mass % KOH aqueous solution, and ion-exchanged water as the balance.

Subsequently, while the liquid phase, of which the temperature was maintained at 20° C., was stirred up in the blending tank 12, a gel agent aqueous solution maintained at 80° C. was poured through the feed pipe 14 extending from the emulsifying tank 11 into the blending tank 12 so that the gel agent aqueous solution was allowed to be cooled and solidified. At this time, the gel agent aqueous solution was poured as a continuous fluid into the liquid phase via an air phase. Before the gel agent aqueous solution was poured, the liquid phase had its viscosity at 20° C. measured with a B-type viscometer (No. 3 Rotor at a rotational frequency of 6 rpm). The viscosity was 20000 mPa·s. The stirring energy while the liquid phase was being stirred up was 5000 kW×second/m³. The mass ratio of the gel agent aqueous solution to the liquid phase is 30/70.

Then, while the mixture continued to be stirred up, a liquid phase including a lump of a solidified product (non-crosslinked hydrogel) obtained by solidifying the gel agent aqueous solution, was discharged through the discharge pipe 15 extending from the blending tank 12 by operating the pump 16. In the meantime, hydrogel particles were formed by allowing the solidified product to be transmitted through, and crushed by, the sieve 17 arranged halfway through the discharge pipe 15 and then were collected in the collection tank 13. The hydrogel particles thus obtained were regarded as Example 1-1. A liquid phase including the hydrogel particles of Examples 1-1 had the volume mean particle size of the hydrogel particles measured by a laser diffraction/scattering method using a laser diffraction/scattering particle size analyzer (LA-920 manufactured by HORIBA, Ltd.). As a result, the mean particle size was 100 μm.

Examples 1-2 and 1-3

Hydrogel particles, produced in the same way as in Example 1-1 except that the solid fat of monoglyceride stearate was replaced with a solid fat of propylene glycol monostearate (Sunsoft No. 25CD manufactured by Taiyo Kagaku Co., Ltd.), were regarded as Example 1-2. Hydrogel particles, produced in the same way as in Example 1-1 except that propylene glycol monobehenate (RIKEMAL PB-100 manufactured by Riken Vitamin Co., Ltd.) was used as an alternative solid fat, were regarded as Example 1-3.

Examples 1-4 to 1-6

Hydrogel particles, produced in the same way as in Example 1-1 except that the solid fat of monoglyceride stearate was partially replaced with a solid fat of monoglyceride succinate (Step SS manufactured by Kao Corporation) and that these components were blended together such that the resultant hydrogel particles would include 10.5 mass % of monoglyceride stearate and 3.0 mass % of monoglyceride succinate, were regarded as Example 1-4.

Hydrogel particles, produced in the same way as in Example 1-1 except that the solid fat of monoglyceride stearate was partially replaced with a liquid oil of octyl para-methoxycinnamate (Uvinul MC80 manufactured by BASF Japan Ltd.) and that these components were blended together such that the resultant hydrogel particles would include 9.0 mass % of monoglyceride stearate and 4.5 mass % of octyl para-methoxycinnamate, were regarded as Example 1-5. Hydrogel particles, produced in the same way as in Example 1-5 except that the components were blended together such that the resultant hydrogel particles would include 3.0 mass % of monoglyceride stearate and 10.5 mass % of octyl para-methoxycinnamate, were regarded as Example 1-6. For each of the hydrogel particles of Examples 1-5 and 1-6, in microscopic images of arbitrarily selected 10 particles, the largest major diameter thereof was divided by the width of its perpendicular bisector, and their average was calculated as an aspect ratio. As a result, the hydrogel particles of Examples 1-5 and 1-6 had an aspect ratio of 3.6 and an aspect ratio of 3.5, respectively.

Examples 1-7 to 1-9

A dispersed particle component liquid of an oil component, including N-(2-hydroxy-3-hexadecyloxypropyl)-N-2-hydroxyethyl hexadecanamide (Sphingolipid E manufactured by Kao Corporation) as a solid fat, dipentaerythritol fatty acid ester (COSMOL ARV manufactured by Nisshin Oillio Group Ltd.) as another solid fat, polyglyceryl diisostearate (COSMOL 42V manufactured by Nisshin Oillio Group Ltd.) as a liquid oil, and methylpolysiloxane (Silicone KF-96A-10cs manufactured by Shin-Etsu Chemical Co., Ltd.) as another liquid oil, was prepared. In this case, these components were blended together such that the resultant hydrogel particles would include 10 mass % of N-(2-hydroxy-3-hexadecyloxypropyl)-N-2-hydroxyethyl hexadecanamide, 2.5 mass % of dipentaerythritol fatty acid ester, 5.0 mass % of polyglyceryl diisostearate, and 5.0 mass % of methylpolysiloxane.

Meanwhile, a hydrogel component aqueous solution, including agar as a gel agent, an acrylic acid-alkyl methacrylate copolymer (PEMULEN TR-1 manufactured by Nikko Chemicals Co., Ltd.) and polyoxyethylene lauryl ether sodium phosphate (SPE-104NB manufactured by Kao Corporation) as dispersants, methyl paraoxy benzoate as an antiseptic agent, a 1N NaOH aqueous solution as a pH adjusting agent, and ion-exchanged water, was also prepared. In this case, these components were blended together so that the resultant hydrogel particles would include 3.0 mass % of agar, 0.04 mass % of acrylic acid-alkyl methacrylate copolymer, 0.05 mass % of polyoxyethylene lauryl ether sodium phosphate, 0.03 mass % of methyl paraoxy benzoate, 0.02 mass % of 1N NaOH aqueous solution, and the ion-exchanged water and other substances as the balance.

Then, the dispersed particle component liquid and the hydrogel component aqueous solution were prepared to have a total weight of 1000 g and a mass ratio of 22.5:77.5, and then dissolved under heat at 80° C. and 90° C., respectively. In this state, in the emulsifying tank 11, the dispersed particle component liquid was added to the hydrogel component aqueous solution. Then, the resultant mixture was stirred up for 1 minute at a rotational frequency of 8000 rpm with a homomixer (T. K. Robomix manufactured by PRIMIX Corporation), thereby preparing a gel agent aqueous solution as an oil-in-water dispersion.

The hydrogel particles, produced in the same way as in Example 1-1 except that this gel agent aqueous solution was used, were regarded as Example 1-7.

Hydrogel particles, produced in the same way as in Example 1-7 except that a hydrogel component aqueous solution prepared so that the resultant hydrogel particles would include 1.0 mass % of agar had been used, were regarded as Example 1-8. Hydrogel particles, produced in the same way as in Example 1-7 except that a hydrogel component aqueous solution prepared so that the resultant hydrogel particles would include 1.5 mass % of agar had been used, were regarded as Example 1-9.

Example 1-10

Hydrogel particles, produced in the same way as in Example 1-1 except that a hydrogel component aqueous solution including no dispersed particle component liquid was used as it was as a gel agent aqueous solution, were regarded as Example 1-10.

Example 1-11

A dispersed particle component liquid of an oil component, including monoglyceride stearate as a solid fat, octyl para-methoxycinnamate as a liquid oil, and diethylamino hydroxybenzoyl hexyl benzoate as a crystalline organic ultraviolet absorbent, was prepared. In this case, these components were blended together so that the resultant hydrogel particles would include 3.0 mass % of monoglyceride stearate, 10.5 mass % of octyl para-methoxycinnamate, and 4.5 mass % of diethylamino hydroxybenzoyl hexyl benzoate.

Meanwhile, a hydrogel component aqueous solution, including agar as a gel agent, an acrylic acid-alkyl methacrylate copolymer and polyvinyl alcohol as dispersants, a 48 mass % NaOH aqueous solution (manufactured by Kishida Chemical Co., Ltd.) as a pH adjusting agent and ion-exchanged water, was also prepared. In this case, these components were blended together so that the resultant hydrogel particles would include 1.5 mass % of agar, 0.1 mass % of acrylic acid-alkyl methacrylate copolymer, 0.5 mass % of polyvinyl alcohol, 0.06 mass % of 48 mass % NaOH aqueous solution, and the ion-exchanged water and other substances as the balance.

Then, the dispersed particle component liquid and the hydrogel component aqueous solution were prepared to have a total weight of 1000 g and a mass ratio of 18:82, and then dissolved under heat at 80° C. and 90° C., respectively. In this state, in the emulsifying tank 11 of the apparatus A, the dispersed particle component liquid was added to the hydrogel component aqueous solution. Then, the resultant mixture was stirred up for 1 minute at a rotational frequency of 8000 rpm with a homomixer (T. K. Robomix manufactured by PRIMIX Corporation), thereby preparing a gel agent aqueous solution as an oil-in-water dispersion. This gel agent aqueous solution had the volume mean particle size of its dispersed particles measured by a laser diffraction/scattering method with a laser diffraction/scattering particle size analyzer (LA-920 manufactured by HORIBA, Ltd.). As a result, the mean particle size was 5 μm. Also, the gel point of this gel agent aqueous solution was measured to be 30° C. or more.

Meanwhile, in the blending tank 12, an acrylic acid-alkyl methacrylate copolymer (PEMULEN TR-2 manufactured by Nikko Chemicals Co., Ltd.) was added as a thickener to, and dissolved in, the ion-exchanged water. Thereafter, the mixture was neutralized with the addition of a 48 mass % KOH aqueous solution (manufactured by Kishida Chemical Co., Ltd.) to prepare 2333 g of a liquid phase. The liquid phase included 0.79 mass % of acrylic acid-alkyl methacrylate copolymer, 0.31 mass % of 48 mass % KOH aqueous solution, and ion-exchanged water as the balance.

Subsequently, while the liquid phase, of which the temperature was maintained at 20° C., was stirred up in the blending tank 12, a gel agent aqueous solution maintained at 80° C. was poured through the feed pipe 14 extending from the emulsifying tank 11 into the blending tank 12 so that the gel agent aqueous solution was allowed to be cooled and solidified. At this time, the gel agent aqueous solution was poured as a continuous fluid into the liquid phase via an air phase. Before the gel agent aqueous solution was poured, the liquid phase had its viscosity at 20° C. measured with a B-type viscometer (No. 3 Rotor at a rotational frequency of 6 rpm). The viscosity was 20000 mPa·s. The stirring energy while the liquid phase was being stirred up was 5000 kW×second/m$^3$. The mass ratio of the gel agent aqueous solution to the liquid phase is 30/70.

Then, while the mixture continued to be stirred up, a liquid phase including a lump of a solidified product (non-crosslinked hydrogel) obtained by solidifying the gel agent aqueous solution, was discharged through the discharge pipe 15 extending from the blending tank 12 by operating the pump 16. In the meantime, hydrogel particles were formed by allowing the solidified product to be transmitted through, and crushed by, the sieve 17 arranged halfway through the discharge pipe 15 and then were collected in the collection tank 13. Hydrogel particles thus obtained were regarded as Example 1-11.

TABLE 1-1

| | | | | | Examples | | | | | |
|---|---|---|---|---|---|---|---|---|---|---|
| | | | | | 1-1 | 1-2 | 1-3 | 1-4 | 1-5 | 1-6 |
| Hydrogel Particles (mass %) | Gel Agent Aqueous Solution | Dispersed Particle Component Liquid | Solid Fat | Monoglyceride Stearate RHEODOL MS-60 by Kao | 13.5 (50.0) <4.05> | | | 10.5 (38.9) <3.15> | 9.0 (33.3) <2.70> | 3.0 (11.1) <0.90> |
| | | | | Propylene Glycol Monostearate Sunsoft No. 25CD by Taiyo Kagaku | | 13.5 (50.0) <4.05> | | | | |
| | | | | Propylene Glycol Monobehenate RIKEMAL PB-100 by Riken Vitamin | | | 13.5 (50.0) <4.05> | | | |
| | | | | Monoglyceride Succinate Step SS by Kao | | | | 3.0 (11.1) <0.90> | | |
| | | | Liquid Oil | Octyl Para-Methoxycinnamate Uvinul MC80 by BASF Japan | | | | | 4.5 (16.7) <1.35> | 10.5 (39.9) <3.15> |
| | | | Ultraviolet Absorbent | Diethylamino Hydroxybenzoyl Hexyl Benzoate Uvinul A Plus by BASF Japan. | 13.5 (50.0) <4.05> | 13.5 (50.0) <4.05> | 13.5 (50.0) <4.05> | 13.5 (50.0) <4.05> | 13.5 (50.0) <4.05> | 13.5 (50.0) <4.05> |

TABLE 1-1-continued

| | | | | | Examples | | | | | |
|---|---|---|---|---|---|---|---|---|---|---|
| | | | | | 1-1 | 1-2 | 1-3 | 1-4 | 1-5 | 1-6 |
| Hydrogel Component Aqueous Solution | Gel Agent | Agar UP-16 by Ina Food Industry | | | 2.0 (2.74) <0.60> | 2.0 (2.74) <0.60> | 2.0 (2.74) <0.60> | 2.0 (2.74) <0.60> | 2.0 (2.74) <0.60> | 2.0 (2.74) <0.60> |
| | Dispersant | Acrylic Acid-Alkyl Methacrylate Copolymer PEMULEN TR-2 by Nikko Chemicals | | | 0.1 (0.14) <0.03> | 0.1 (0.14) <0.03> | 0.1 (0.14) <0.03> | 0.1 (0.14) <0.03> | 0.1 (0.14) <0.03> | 0.1 (0.14) <0.03> |
| | | Polyvinyl Alcohol GOHSENOL EG-05 by Nippon Synthetic Chemical Industry | | | 0.5 (0.68) <0.15> | 0.5 (0.68) <0.15> | 0.5 (0.68) <0.15> | 0.5 (0.68) <0.15> | 0.5 (0.68) <0.15> | 0.5 (0.68) <0.15> |
| | pH Adjusting Agent | 1N NaOH by Kishida Chemical | | | 0.75 (1.03) <0.23> | 0.75 (1.03) <0.23> | 0.75 (1.03) <0.23> | 0.75 (1.03) <0.23> | 0.75 (1.03) <0.23> | 0.75 (1.03) <0.23> |
| | Water | Ion Exchanged Water | | | Bal. | Bal. | Bal. | Bal. | Bal. | Bal. |

*The numeral in parentheses on the middle row indicates its content either in the dispersed particle component liquid or hydrogel component aqueous solution. The numeral in parentheses on the bottom row indicates its content in the liquid phase including the hydrogel particles.

TABLE 1-2

| | | | | | Examples | | | | |
|---|---|---|---|---|---|---|---|---|---|
| | | | | | 1-7 | 1-8 | 1-9 | 1-10 | 1-11 |
| Hydrogel Particles (mass %) | Gel Agent Aqueous Solution | Dispersed Particle Component Liquid | Solid Fat | Monoglyceride Stearate RHEODOL MS-60 by Kao | | | | | 3.0 (16.7) <0.90> |
| | | | | N-(2-Hydroxy-3-Hexadecyloxypropyl)-N-2-Hydroxyethyl Hexadecanamide Sphingolipid E by Kao | 10.0 (44.4) <3.00> | 10.0 (44.4) <3.00> | 10.0 (44.4) <3.00> | | |
| | | | | Dipentaerythritol Fatty Acid Ester COSMOL ARV by Nisshin Oillio Group | 2.5 (11.1) <0.75> | 2.5 (11.1) <0.75> | 2.5 (11.1) <0.75> | | |
| | | | Liquid Oil | Octyl Para-Methoxycinnamate Uvinul MC80 by BASF Japan | | | | | 10.5 (58.3) <3.15> |
| | | | | Polyglyceryl Diisostearate COSMOL 42V by Nisshin Oillio Group | 5.0 (22.2) <1.50> | 5.0 (22.2) <1.50> | 5.0 (22.2) <1.50> | | |
| | | | | Methylpolysiloxane Silicone KF-96A-10cs by Shin-Etsu Chemical | 5.0 (22.2) <1.50> | 5.0 (22.2) <1.50> | 5.0 (22.2) <1.50> | | |
| | | | Ultraviolet Absorbent | Diethylamino Hydroxybenzoyl Hexyl Benzoate Uvinul A Plus by BASF Japan | | | | | 4.5 (25.0) <1.35> |
| | Hydrogel Component Aqueous Solution | Gel Agent | | Agar UP-16 by Ina Food Industry | 3.0 (3.87) <0.90> | 1.0 (1.29) <0.30> | 1.5 (1.94) <0.45> | 1.5 (1.5) <0.45> | 1.5 (1.8) <0.45> |
| | | Dispersant | | Acrylic Acid-Alkyl Methacrylate Copolymer PEMULEN TR-2 by Nikko Chemicals | | | | 0.1 (0.1) <0.03> | 0.1 (0.12) <0.03> |
| | | | | Acrylic Acid-Alkyl Methacrylate Copolymer PEMULEN TR-1 by Nikko Chemicals | 0.04 (0.05) <0.01> | 0.04 (0.05) <0.01> | 0.04 (0.05) <0.01> | | |
| | | | | Polyoxyethylene Lauryl Ether Sodium Phosphate SPE-104NB by Kao | 0.05 (0.06) <0.02> | 0.05 (0.06) <0.02> | 0.05 (0.06) <0.02> | | |
| | | | | Polyvinyl Alcohol GOHSENOL EG-05 by Nippon Synthetic Chemical Industry | | | | 0.5 (0.5) <0.15> | 0.5 (0.61) <0.15> |

TABLE 1-2-continued

|  |  |  | Examples | | | | |
|---|---|---|---|---|---|---|---|
|  |  |  | 1-7 | 1-8 | 1-9 | 1-10 | 1-11 |
| Antiseptic Agent | Methyl Paraoxy Benzoate | | 0.03 (0.04) <0.01> | 0.03 (0.04) <0.01> | 0.03 (0.04) <0.01> | | |
| pH Adjusting Agent | 1N NaOH by Kishida Chemical | | 0.02 (0.03) <0.01> | 0.02 (0.03) <0.01> | 0.02 (0.03) <0.01> | 0.75 (0.75) <0.23> | |
|  | 48% NaOH by Kishida Chemical | | | | | | 0.06 (0.07) <0.02> |
| Water | Ion Exchanged Water | | Bal. | Bal. | Bal. | Bal. | Bal. |

*The numeral in parentheses on the middle row indicates its content either in the dispersed particle component liquid or hydrogel component aqueous solution.
The numeral in parentheses on the bottom row indicates its content in the liquid phase including the hydrogel particles.

TABLE 1-3

|  |  |  | Examples 1-1-1-11 |
|---|---|---|---|
| Liquid Phase (mass %) | Thickener | Acrylic Acid-Alkyl Methacrylate Copolymer PEMULEN TR-2 by Nikko Chemicals | 0.79 |
|  | pH Adjusting Agent | 48% KOH by Kishida Chemical | 0.31 |
|  | Water | Ion Exchanged Water | Balance |
| Liquid Phase's Viscosity (mPa · s) | | | 20000 |

Second Example

Hydrogel particles representing the following Examples 2-1 to 2-7 were produced with the apparatus A shown in FIG. 2. The specifics of those examples are also shown in Tables 2-1 and 2-2.

Example 2-1

Hydrogel particles, produced in the same way as in Example 1-11 except that the mass ratio of the gel agent aqueous solution to the liquid phase was set to be 5/95 and that a gel agent aqueous solution maintained at 60° C. was poured into a liquid phase, of which the temperature was set to be 30° C., and then cooled, were regarded as Example 2-1. Before the gel agent aqueous solution was poured, the liquid phase had its viscosity at 20° C. measured with a B-type viscometer (No. 3 Rotor at a rotational frequency of 6 rpm). The viscosity was 20000 mPa·s.

Examples 2-2 and 2-3

Hydrogel particles, produced in the same way as in Example 2-1 except that the temperature of the liquid phase was set to be 20° C., were regarded as Example 2-2. Hydrogel particles, produced in the same way as in Example 2-1 except that the temperature of the liquid phase was set to be 10° C., were regarded as Example 2-3.

Examples 2-4 and 2-5

Hydrogel particles, produced in the same way as in Example 2-2 except that the gel agent aqueous solution was maintained at 50° C., were regarded as Example 2-4. Hydrogel particles, produced in the same way as in Example 2-2 except that the gel agent aqueous solution was maintained at 40° C., were regarded as Example 2-5.

Example 2-6

Hydrogel particles, produced in the same way as in Example 2-1 except that a gel agent aqueous solution maintained at 40° C. was poured into a liquid phase, of which the temperature was set to be 10° C., and then cooled, were regarded as Example 2-6.

Example 2-7

Hydrogel particles, produced in the same way as in Example 2-1 except that a gel agent aqueous solution maintained at 80° C. was poured into a liquid phase, of which the temperature was set to be 15° C., and then cooled, were regarded as Example 2-7.

TABLE 2-1

|  |  |  |  |  | Examples 2-1-2-7 |
|---|---|---|---|---|---|
| Hydrogel Particles (mass %) | Gel Agent Aqueous Solution | Dispersed Particle Component Liquid | Solid Fat | Monoglyceride Stearate RHEODOL MS-60 by Kao | 3.0 (16.7) <0.15> |
|  |  |  | Liquid Oil | Octyl Para-Methoxycinnamate | 10.5 (58.3) |
|  |  |  |  | Uvinul MC80 by BASF Japan | <0.53> |

TABLE 2-1-continued

|  |  |  | Examples 2-1-2-7 |
|---|---|---|---|
|  | Ultraviolet Absorbent | Diethylamino Hydroxybenzoyl Hexyl Benzoate Uvinul A Plus by BASF Japan | 4.5 (25.0) <0.23> |
| Hydrogel Component Aqueous Solution | Gel Agent | Agar UP-16 by Ina Food Industry | 1.5 (1.8) <0.08> |
|  | Dispersant | Acrylic Acid-Alkyl Methacrylate Copolymer PEMULEN TR-2 by Nikko Chemicals | 0.1 (0.12) <0.01> |
|  |  | Polyvinyl Alcohol GOHSENOL EG-05 by Nippon Synthetic Chemical Industry | 0.5 (0.61) <0.03> |
|  | pH Adjusting Agent | 48% NaOH by Kishida Chemical | 0.06 (0.07) <0.01> |
|  | Water | Ion Exchanged Water | Balance |

* The numeral in parentheses on the middle row indicates its content either in the dispersed particle component liquid or hydrogel component aqueous solution.
The numeral in parentheses on the bottom row indicates its content in the liquid phase including the hydrogel particles.

As for the hydrogel particles representing Examples 2-1 to 2-7, diethylamino hydroxybenzoyl hexyl benzoate (Uvinul A plus manufactured by BASF Japan Ltd.) as a crystalline organic ultraviolet absorbent was quantified by an HPLC method in an ordinary manner, thereby obtaining, as a residual ratio, the ratio of the mass of the ultraviolet absorbent to the mass of the absorbent added to the dispersed particle component liquid. The residual ratios of the hydrogel particles representing Examples 2-1 to 2-7 are shown in the following Table 2-2.

TABLE 2-2

|  | Examples |  |  |  |  |  |  |
|---|---|---|---|---|---|---|---|
|  | 2-1 | 2-2 | 2-3 | 2-4 | 2-5 | 2-6 | 2-7 |
| Gel Agent Aqueous Solution's Temperature (° C.) | 60 | 60 | 60 | 50 | 40 | 40 | 80 |
| Liquid Phase's Temperature (° C.) | 30 | 20 | 10 | 20 | 20 | 10 | 15 |
| Hydrogel Particles' Residual Ratio (%) | 88.0 | 95.6 | 100 | 92.1 | 83.7 | 100 | 97.1 |

Third Example

Hydrogel particles representing the following Examples 3-1 to 3-3 were produced with the apparatus A shown in FIG. 2. The specifics of those examples are also shown in Tables 3-1 to 3-3.

Example 3-1

Hydrogel particles, produced in the same way as in Example 1-11 except that 2000 g of an aqueous solution, which had been blended to include 0.79 mass % of acrylic acid-alkyl methacrylate copolymer, 0.31 mass % of 48 mass % KOH aqueous solution, and the ion exchanged water as the balance, was used as a liquid phase, that the mass ratio of the gel agent aqueous solution to the liquid phase was set to be 5/95 and that a gel agent aqueous solution maintained at 60° C. was poured into a liquid phase, of which the temperature was set to be 15° C., and then cooled, were regarded as Example 3-1. Before the gel agent aqueous solution was poured, the liquid phase used to produce Example 3-1 had its viscosity at 20° C. measured with a B-type viscometer (No. 3 Rotor at a rotational frequency of 6 rpm). As a result, the liquid phase had a viscosity of 20000 mPa·s.

Examples 3-2 and 3-3

Hydrogel particles, produced in the same way as in Example 3-1 except that the content of the ion exchanged water was decreased by 15 mass % compared to Example 3-1 and that 1700 g of an aqueous solution, which had been blended to include 0.93 mass % of acrylic acid-alkyl methacrylate copolymer, 0.37 mass % of 48 mass % KOH aqueous solution, and the ion exchanged water as the balance, was used as a liquid phase, were regarded as Example 3-2. Before the gel agent aqueous solution was poured, the liquid phase used to produce Example 3-2 had its viscosity at 20° C. measured with a B-type viscometer (No. 3 Rotor at a rotational frequency of 6 rpm). As a result, the liquid phase had a viscosity of 25750 mPa·s.

Hydrogel particles, produced in the same way as in Example 3-1 except that the content of the ion exchanged water was decreased by 30 mass % compared to Example 3-1 and that 1400 g of an aqueous solution, which had been blended to include 1.13 mass % of acrylic acid-alkyl methacrylate copolymer, 0.45 mass % of 48 mass % KOH aqueous solution, and the ion exchanged water as the balance, was used as a liquid phase, were regarded as Example 3-3. Before the gel agent aqueous solution was poured, the liquid phase used to produce Example 3-3 had its viscosity at 20° C. measured with a B-type viscometer (No. 3 Rotor at a rotational frequency of 6 rpm). As a result, the liquid phase had a viscosity of 37000 mPa·s.

TABLE 3-1

|  |  |  |  |  | Examples 3-1-3-3 |
|---|---|---|---|---|---|
| Hydrogel Particles (mass %) | Gel Agent Aqueous Solution | Dispersed Particle Component Liquid | Solid Fat | Monoglyceride Stearate RHEODOL MS-60 by Kao | 3.0 (16.7) <0.15> |
|  |  |  | Liquid Oil | Octyl Para-Methoxycinnamate Uvinul MC80 by BASF Japan | 10.5 (58.3) <0.53> |
|  |  |  | Ultraviolet Absorbent | Diethylamino Hydroxybenzoyl Hexyl Benzoate Uvinul A Plus by BASF Japan | 4.5 (25.0) <0.23> |
|  |  | Hydrogel Component Aqueous Solution | Gel Agent | Agar UP-16 by Ina Food Industry | 1.5 (1.8) <0.08> |
|  |  |  | Dispersant | Acrylic Acid-Alkyl Methacrylate Copolymer PEMULEN TR-2 by Nikko Chemicals | 0.1 (0.12) <0.01> |
|  |  |  |  | Polyvinyl Alcohol GOHSENOL EG-05 by Nippon Synthetic Chemical Industry | 0.5 (0.61) <0.03> |
|  |  |  | pH Adjusting Agent | 48% NaOH by Kishida Chemical | 0.06 (0.07) <0.01> |
|  |  |  | Water | Ion Exchanged Water | Balance |

* The numeral in parentheses on the middle row indicates its content either in the dispersed particle component liquid or hydrogel component aqueous solution.
The numeral in parentheses on the bottom row indicates its content in the liquid phase including the hydrogel particles.

TABLE 3-2

|  |  |  | Examples |  |  |
|---|---|---|---|---|---|
|  |  |  | 3-1 | 3-2 | 3-3 |
| Liquid Phase (mass %) | Thickener | Acrylic Acid-Alkyl Methacrylate Copolymer PEMULEN TR-2 by Nikko Chemicals | 0.79 | 0.93 | 1.13 |
|  | pH Adjusting Agent | 48% KOH by Kishida Chemical | 0.31 | 0.37 | 0.45 |
|  | Water | Ion Exchanged Water | Bal. | Bal. | Bal. |
| Liquid Phase's Viscosity (mPa · s) |  |  | 20000 | 25750 | 37000 |

The residual ratios of the hydrogel particles representing Examples 3-1 to 3-3, which were obtained in the same way as in the second example, are shown in the following Table 3-3:

TABLE 3-3

|  | Examples |  |  |
|---|---|---|---|
|  | 3-1 | 3-2 | 3-3 |
| Liquid Phase's Viscosity (mPa · s) | 20000 | 25750 | 37000 |

TABLE 3-3-continued

|  | Examples |  |  |
|---|---|---|---|
|  | 3-1 | 3-2 | 3-3 |
| Hydrogel Particles' Residual Ratio (%) | 92.1 | 98.1 | 98.8 |

Fourth Example

Cosmetic products representing the following Examples 4-1 to 4-7 were produced with the apparatus A shown in FIG. 2. The specifics of those examples are also shown in Tables 4-1 to 4-3.

Example 4-1

Lauryl methacrylate-ethylene glycol dimethacrylate-sodium methacrylate copolymer (spherical particles having a mean particle size of 2.2 μm), ethanol, ethylhexyl methoxycinnamate, (2,4-bis-[{4-(2-ethylhexoxy)-2-hydroxy}-phenyl]-6-(4-methoxyphenyl)-1,3,5-triazine), dimethicone, and an acrylic acid-alkyl methacrylate copolymer were added to, and dissolved in, purified water. Then, the mixture was neutralized with the addition of a 48 mass % KOH aqueous solution. Subsequently, a perfume was further added to the mixture, thereby preparing a cosmetic composition liquid phase. In the liquid phase, the lauryl methacrylate-ethylene glycol dimethacrylate-sodium methacrylate copolymer had a content of 2.9 mass %, ethanol had a content of 4.5 mass %, ethylhexyl methoxycinnamate had a content of 10.0 mass %, (2,4-bis-[{4-(2-ethylhexoxy)-2-hydroxy}-phenyl]-6-(4-methoxyphenyl)-1,3,5-triazine) had a content of 2.1 mass %, dimethicone had a content of 2.9 mass %, the acrylic acid-alkyl methacrylate copolymer had a content of 0.54 mass %, KOH had a content of 0.14 mass %, the perfume was added to an adequate quantity, and the ion-exchanged water was the balance thereof.

Hydrogel particles were produced in the same way as in Example 1-11 except that this cosmetic composition liquid phase was used, that the stirring energy while the liquid phase was being stirred up was 858 kW×second/m$^3$, that the mass ratio of the gel agent aqueous solution to the liquid phase was set to be 5/95 and that a gel agent aqueous solution maintained at 60° C. was poured into a liquid phase, of which the temperature was set to be 15° C., and then cooled. A cosmetic product comprised of a cosmetic product composition liquid phase including the hydrogel particles was regarded as Example 4-1. Before the gel agent aqueous solution was poured, the liquid phase had its viscosity at 20° C. measured with a B-type viscometer (No. 3 Rotor at a rotational frequency of 6 rpm). As a result, the liquid phase had a viscosity of 13500 mPa·s.

Examples 4-2 to 4-7

Cosmetic products, produced in the same way as in Example 4-1 except that the stirring energies while the liquid phase was being stirred up were set to be 1469 kW×second/m$^3$, 2969 kW×second/m$^3$, 5219 kW×second/m$^3$, 7733 kW×second/m$^3$, 12932 kW×second/m$^3$, and 25865 kW×second/m$^3$, respectively, were regarded as Examples 4-2 to 4-7.

TABLE 4-1

| | | | | | | Examples 4-1-4-7 |
|---|---|---|---|---|---|---|
| Hydrogel Particles (mass %) | Gel Agent Aqueous Solution | Dispersed Particle Component Liquid | Solid Fat | Monoglyceride Stearate RHEODOL MS-60 by Kao | | 3.0 (16.7) <0.15> |
| | | | Liquid Oil | Octyl Para-Methoxycinnamate Uvinul MC80 by BASF Japan | | 10.5 (58.3) <0.53> |
| | | | Ultraviolet Absorbent | Diethylamino Hydroxybenzoyl Hexyl Benzoate Uvinul A Plus by BASF Japan | | 4.5 (25.0) <0.23> |
| | | Hydrogel Component Aqueous Solution | Gel Agent | Agar UP-16 by Ina Food Industry | | 1.5 (1.8) <0.08> |
| | | | Dispersant | Acrylic Acid-Alkyl Methacrylate Copolymer PEMULEN TR-2 by Nikko Chemicals | | 0.1 (0.12) <0.01> |
| | | | | Polyvinyl Alcohol GOHSENOL EG-05 by Nippon Synthetic Chemical Industry | | 0.5 (0.61) <0.03> |
| | | | | 48% NaOH by Kishida Chemical | | 0.06 (0.07) <0.01> |
| | | | Water | Ion Exchanged Water | | Balance |

* The numeral in parentheses on the middle row indicates its content either in the dispersed particle component liquid or hydrogel component aqueous solution.
The numeral in parentheses on the bottom row indicates its content in the liquid phase including the hydrogel particles.

TABLE 4-2

| | | Examples 4-1-4-7 |
|---|---|---|
| Liquid Phase (mass %) | Lauryl Methacrylate-Ethylene Glycol Dimethacrylate-Sodium Methacrylate Copolymer (Spherical Particles Having a Mean Particle Size of 2.2 μm) | 2.9 (2.8) |
| | Ethanol | 4.5 (4.3) |
| | Ethylhexyl Methoxycinnamate | 10.0 (9.5) |
| | (2,4-bis-[{4-(2-Ethylhexoxy)-2-Hydroxy}-Phenyl]-6-(4-Methoxyphenyl)-1,3,5-Triazine) | 2.1 (2.0) |
| | Dimethicone | 2.9 (2.8) |
| | Acrylic Acid-Alkyl Methacrylate Copolymer | 0.54 (0.51) |
| | KOH | 0.14 (0.13) |
| | Perfume | Appropriate quantity |
| | Purified Water | Balance |
| Gel Agent Aqueous Solution (Hydrogel Particles) (mass %) | | — (5.0) |

* The numeral in parentheses indicates its content in the liquid phase including the gel agent aqueous solution (hydrogel particles).

The residual ratios of the hydrogel particles representing Examples 4-1 to 4-7, which were obtained in the same way as in the second example, are shown in the following Table 4-3.

TABLE 4-3

|  | Examples | | | | | | |
| --- | --- | --- | --- | --- | --- | --- | --- |
|  | 4-1 | 4-2 | 4-3 | 4-4 | 4-5 | 4-6 | 4-7 |
| Stirring Energy (kW second/m$^3$) | 858 | 1469 | 2969 | 5219 | 7733 | 12932 | 25865 |
| Hydrogel Particles' Residual Ratio (%) | 100 | 98.7 | 98.3 | 94.0 | 78.0 | 73.2 | 67.8 |

As can be seen from the foregoing description, the method for producing hydrogel particles according to the first to fourth examples described above does not need any special manufacturing equipment such as the spray nozzle disclosed in Patent Document 1 and does not require slow cooling as in the method disclosed in Patent Documents 2 and 3, thus achieving high productivity. In addition, this method allows a solidified product of a gel agent aqueous solution to be obtained in a liquid phase, thus alleviating the load in crushing and making it possible to produce hydrogel particles cost-effectively and easily.

INDUSTRIAL APPLICABILITY

The present invention is useful in the fields of a method for producing hydrogel particles, a method for producing a cosmetic product, and an apparatus for use in these methods.

DESCRIPTION OF REFERENCE CHARACTERS

A Apparatus
11 Emulsifying Tank
12 Blending Tank
13 Collection Tank
14 Feed Pipe
15 Discharge Pipe
16 Pump
17 Sieve

The invention claimed is:

1. A method for producing hydrogel particles, the method comprising the steps of:
dissolving a gel agent forming a non-crosslinked hydrogel in an aqueous solution, said aqueous solution of said gel agent having a gel point of 30° C. or more, and putting the aqueous solution into a liquid phase having a temperature of equal to or lower than the gel point, thereby solidifying said aqueous solution to form a solidified product; and subsequently
crushing the solidified product obtained by solidifying the aqueous solution in which the gel agent is dissolved.

2. The method of claim 1, wherein crushing the solidified product is performed by transmitting, through a sieve, the liquid phase including the solidified product.

3. The method of claim 1, comprising stirring up the liquid phase into which the aqueous solution, in which the gel agent is dissolved, has been put.

4. The method of claim 1, comprising putting, as a continuous fluid, the aqueous solution in which the gel agent is dissolved into the liquid phase.

5. The method of claim 1, comprising putting the aqueous solution in which the gel agent is dissolved into the liquid phase via a gas phase.

6. The method of claim 1, wherein the liquid phase has a viscosity of 1 mPa·s or more.

7. The method of claim 1, wherein the liquid phase is an aqueous phase.

8. The method of claim 1, wherein the aqueous solution in which the gel agent is dissolved is a dispersion in which dispersed particles are distributed.

9. The method of claim 1, wherein a mass ratio of the aqueous solution in which the gel agent is dissolved to the liquid phase is in the range of 1/99 to 50/50.

10. The method of claim 1, wherein the hydrogel particles have an aspect ratio of 1.1 to 20.

11. A method for producing a cosmetic product, the method comprising the steps of:
solidifying an aqueous solution in which a gel agent forming a non-crosslinked hydrogel is dissolved and which has a gel point of 30° C. or more by putting the aqueous solution into a liquid phase having a temperature of equal to or lower than the gel point; and
crushing a solidified product included in the liquid phase and obtained by solidifying the aqueous solution in which the gel agent is dissolved.

12. The method of claim 11, comprising adding a cosmetic component in advance to the liquid phase into which the aqueous solution in which the gel agent is dissolved is yet to be put.

13. The method of claim 12, wherein the liquid phase is an emulsified liquid including the cosmetic component as emulsifying particles.

14. The method of claim 11, comprising adding a cosmetic component to the liquid phase into which the aqueous solution in which the gel agent is dissolved has been put.

15. The method of claim 14, comprising adding the cosmetic component to the liquid phase after the solidified product has been crushed.

* * * * *